United States Patent
Hai et al.

(10) Patent No.: US 9,895,468 B2
(45) Date of Patent: Feb. 20, 2018

(54) IMMOBILIZATION OF AN ACTIVE AGENT ON A SUBSTRATE

(71) Applicants: BAXTER INTERNATIONAL INC., Deerfield, IL (US); BAXTER HEALTHCARE SA, Glattpark (Opfikon) (CH); NORTHWESTERN UNIVERSITY, Evanston, IL (US)

(72) Inventors: Ton That Hai, Round Lake, IL (US); John-Bruce Devault Green, Buffalo Grove, IL (US); Timothy Michael Fulghum, Lakemoor, IL (US); Phillip Byron Messersmith, Clarendon Hills, IL (US); Tadas Stanislovas Sileika, Northbrook, IL (US)

(73) Assignees: BAXTER INTERNATIONAL INC., Deerfield, IL (US); BAXTER HEALTHCARE SA, Glattpark (Opfikon) (CH); NORTHWESTERN UNIVERSITY, Evanston, IL (US)

(*) Notice: Subject to any disclaimer, the term of this patent is extended or adjusted under 35 U.S.C. 154(b) by 0 days.

(21) Appl. No.: 15/449,752

(22) Filed: Mar. 3, 2017

(65) Prior Publication Data
US 2017/0173226 A1   Jun. 22, 2017

Related U.S. Application Data

(62) Division of application No. 14/212,325, filed on Mar. 14, 2014.

(60) Provisional application No. 61/798,765, filed on Mar. 15, 2013.

(51) Int. Cl.
| | |
|---|---|
| A61L 29/16 | (2006.01) |
| A61L 29/08 | (2006.01) |
| A61L 33/06 | (2006.01) |
| A61L 33/04 | (2006.01) |
| A61L 33/00 | (2006.01) |
| A61L 29/06 | (2006.01) |

(52) U.S. Cl.
CPC .......... *A61L 33/0017* (2013.01); *A61L 29/06* (2013.01); *A61L 29/085* (2013.01); *A61L 29/16* (2013.01); *A61L 33/0094* (2013.01); *A61L 33/04* (2013.01); *A61L 33/068* (2013.01); *A61L 2300/42* (2013.01); *A61L 2420/02* (2013.01)

(58) Field of Classification Search
None
See application file for complete search history.

(56) References Cited

U.S. PATENT DOCUMENTS

| | | |
|---|---|---|
| 3,425,418 A | 2/1969 | Chvapil |
| 4,051,302 A | 9/1977 | Mayama et al. |
| 5,242,432 A | 9/1993 | DeFrank |
| 5,360,413 A | 11/1994 | Leason et al. |
| 5,730,418 A | 3/1998 | Feith et al. |
| 5,782,816 A | 7/1998 | Werschmidt et al. |
| 6,039,302 A | 3/2000 | Cote, Sr. et al. |
| 6,669,681 B2 | 12/2003 | Jepson et al. |
| 6,682,509 B2 | 1/2004 | Lopez |
| 7,618,937 B2 | 11/2009 | Messersmith et al. |
| 7,622,533 B2 | 11/2009 | Lee |
| 7,682,669 B1 * | 3/2010 | Michal ............. A61L 31/10 427/2.24 |
| 8,119,742 B2 | 2/2012 | Dalsin et al. |
| 9,125,973 B2 | 9/2015 | Bui et al. |
| 2003/0141477 A1 | 7/2003 | Miller |
| 2003/0208165 A1 | 11/2003 | Christensen et al. |

(Continued)

FOREIGN PATENT DOCUMENTS

| | | |
|---|---|---|
| CN | 101801429 A | 8/2010 |
| CN | 102834123 A | 12/2012 |

(Continued)

OTHER PUBLICATIONS

Agarwal et al., Gallic acid causes inactivating phosphorylation of cdc25A/cdc25C-cdc2 via ATM-Chk2 activation, leading to cell cycle arrest, and induces apoptosis in human prostate carcinoma DU145 cells, Mol. Cancer Ther., 5(12):3294-302 (2006).

Chen et al., A simple one-step modification of various materials for introducing effective multifunctional groups, Colloids Surf. B Biointerfaces, 113:125-33 (2014).

Davis et al., Immobilization of RGD to < 1 1 1 > silicon surfaces for enhanced cell adhesion and proliferation, Biomaterials 23(19):4019-27 (2002).

Dorniani et al., Preparation of $Fe_3O_4$ magnetic nanoparticles coated with gallic acid for drug delivery, Int. J. Nanomedicine, 7:5745-56 (2012).

(Continued)

*Primary Examiner* — Robert A Wax
*Assistant Examiner* — Danah Al-Awadi
(74) *Attorney, Agent, or Firm* — Marshall, Gerstein & Borun LLP

(57) ABSTRACT

The invention provides methods of immobilizing an active agent to a substrate surface, including the steps of, depositing a primer compound on a substrate, thereby forming a primed substrate, contacting the primed substrate with a solution of a compound including a trihydroxyphenyl group, thereby forming a trihydroxyphenyl-treated primed substrate, and contacting the trihydroxyphenyl-treated primed substrate with a solution of an active agent, thereby immobilizing the active agent on the substrate. Further provided are methods of immobilizing an active agent on a substrate, including the steps of providing a substrate, combining a solution of a compound including a trihydroxyphenyl group with a solution of an active agent, thereby forming a solution of an active agent-trihydroxyphenyl conjugate, and contacting the primed substrate with the solution of the active agent-trihydroxyphenyl conjugate, thereby immobilizing the active agent on the substrate. The invention further provides substrates and medical device or device components with active agents immobilized on the surface thereof.

19 Claims, 2 Drawing Sheets

(56) References Cited

U.S. PATENT DOCUMENTS

| | | |
|---|---|---|
| 2006/0009550 A1 | 1/2006 | Messersmith et al. |
| 2007/0282422 A1 | 12/2007 | Biggs et al. |
| 2008/0021381 A1 | 1/2008 | Lurvey et al. |
| 2008/0021392 A1 | 1/2008 | Lurvey et al. |
| 2008/0169059 A1 | 7/2008 | Messersmith et al. |
| 2008/0247984 A1 | 10/2008 | Messersmith et al. |
| 2009/0024096 A1 | 1/2009 | Hai et al. |
| 2009/0105629 A1 | 4/2009 | Grant et al. |
| 2009/0123652 A1 | 5/2009 | Messersmith et al. |
| 2010/0028719 A1 | 2/2010 | Messersmith et al. |
| 2010/0063153 A1 | 3/2010 | Chatterjee et al. |
| 2010/0113828 A1 | 5/2010 | Dalsin et al. |
| 2010/0137902 A1 | 6/2010 | Lee et al. |
| 2010/0137903 A1 | 6/2010 | Lee et al. |
| 2010/0197868 A1 | 8/2010 | Lee |
| 2010/0297745 A1 | 11/2010 | Li et al. |
| 2011/0009955 A1 | 1/2011 | Horres et al. |
| 2011/0046255 A1 | 2/2011 | Rooijmans |
| 2011/0065085 A1* | 3/2011 | Biran .................. A61L 27/54 435/4 |
| 2012/0116424 A1 | 5/2012 | Lee et al. |
| 2012/0149849 A1 | 6/2012 | Dalsin et al. |
| 2013/0052236 A1* | 2/2013 | Tessmar .................. A61L 31/10 424/400 |
| 2013/0224795 A1* | 8/2013 | Park ................. A61K 47/48192 435/68.1 |
| 2014/0364391 A1 | 12/2014 | Hai et al. |

FOREIGN PATENT DOCUMENTS

| | | |
|---|---|---|
| EP | 1043720 A1 | 10/2000 |
| EP | 1829566 A1 | 9/2007 |
| JP | 2007-527871 A | 10/2007 |
| JP | 2008253707 A | 10/2008 |
| JP | 2010-189649 A | 9/2010 |
| WO | WO-2012064821 A2 | 5/2012 |
| WO | WO-2012/113058 | 8/2012 |
| WO | WO-2012/158944 A1 | 11/2012 |
| WO | WO-2013/053809 A1 | 4/2013 |

OTHER PUBLICATIONS

Ebara et al., Surface modification of microfluidic channels by UV-mediated graft polymerization of non-fouling and "smart" polymers, Radiation Physics and Chem., 76(8-9):1409-13 (2007).

Ebara et al., Switchable surface traps for injectable bead-based chromatography in PDMS microfluidic channels, Lab Chip, 6(7):843-8 (2006).

Faried et al., Anticancer effects of gallic acid isolated from Indonesian herbal medicine, Phaleria macrocarpa (Scheff.) Boerl, on human cancer cell lines, Int. J. Oncol., 30(3):605-13 (2007).

First Office Action (with English translation), Chinese patent application No. 201480015897.3, issued Sep. 21, 2016.

Goda et al., Biomimetic phosphorylcholine polymer grafting from polydimethylsiloxane surface using photo-induced polymerization, Biomaterials, 27(3):5151-60 (2006).

Goda et al., Photografting of 2-methacryloyloxyethyl phosphorylcholine from polydimethylsiloxane: Tunable protein repellency and lubrication property, Colloids and Surfaces B: Biointerfaces, 63(1):64-72 (2008).

Hu et al., Surface modification of poly(dimethylsiloxane) microfluidic devices by ultraviolet polymer grafting, Anal. Chem., 74(16):4117-23 (2002).

Hu et al., Surface-directed, graft polymerization within microfluidic channels, Anal. Chem., 76(7)1 865-70 (2004).

Inoue et al., Role of reactive oxygen species in gallic acid-induced apoptosis, Biol. Pharm. Bull., 23(10):1153-7 (2000).

International Preliminary Report on Patentability, International Application No. PCT/US2014/027466, dated Jul. 9, 2015.

International Search Report and Written Opinion, corresponding International Application No. PCT/US2014/027466, dated Aug. 6, 2014.

Kang et al., Inhibitory effect of methyl gallate and gallic acid on oral bacteria, J. Microbiol., 46(6):744-50 (2008).

Kaur et al., Gallic acid, an active constituent of grape seed extract, exhibits anti-proliferative, pro-apoptotic and anti-tumorigenic effects against prostate carcinoma xenograft growth in nude mice, Pharm. Res., 26(9):2133-40 (2009).

Kawada et al., Anti-tumor effect of gallic acid on LL-2 lung cancer cells transplanted in mice, Anticancer Drugs, 12(10):847-52 (2001).

Kim et al., Gallic acid inhibits histamine release and pro-inflammatory cytokine production in mast cells, Toxicol. Sci., 91(1):123-31 (2006).

Kratz et al., Evaluation of anti-HSV-2 activity of gallic acid and pentyl gallate, Biol. Pharm. Bull., 31(5):903-7 (2008).

Luo et al., Improved immobilization of biomolecules to quinone-rich polydopamine for efficient surface functionalization, Colloids Surf. B. Biointerfaces, 106:66-73 (2013).

Luo et al., In vitro investigation of enhanced hemocompatibility and endothelial cell proliferation associated with quinone-rich polydopamine coating, ACS Appl. Mater. Interfaces, 5(5):1704-14 (2013).

Ma et al., Preparation and characterization of thermo-responsive PDMS surfaces grafted with poly(N-isopropylacrylamide) by benzophenone-initiated photopolymerization, J. Colloid Interface Sci., 332(1):85-90 (2009).

Mourya et al., Chitosan modifications and applications: Opportunities galore, Reactive Functional Polymers, 68(6):1013-51 (2008).

Ohno et al., Induction of apoptosis by gallic acid in lung cancer cells, Anticancer Drugs, 10(9):845-51 (1999).

Rajalakshmi et al., Assessment of the no-observed-adverse-effect level (NOAEL) of gallic acid in mice, Food Chem. Toxicol., 39(9):919-22 (2001).

Serrano et al., Double-edged sword behaviour of gallic acid and its interaction with peroxidases in human microvascular endothelial cell culture (HMEC-1). Antioxidant and pro-oxidant effects, Acta Bichim. Pol., 57(2):193-8 (2010).

Strlic et al., Anti- and prooxidative properties of gallic acid in fenton-type systems, J. Agric. Food Chem., 50(22):6313-7 (2002).

Sui et al., Solution-phase surface modification in intact poly(dimethylsiloxane) microfluidic channels, Anal. Chem., 78(15):5543-51 (2006).

Vartiainen et al., Tyorsinase-catalysed grafting of food-grade gallates to chitosan: surface properties of novel functional coatings, Packaging Technology and Science, 21(6):317-28 (2008).

Veluri et al., Fractionation of grape seed extract and identification of gallic acid as one of the major active constituents causing growth inhibition and apoptotic death of DU145 human prostate carcinoma cells, Carcinogenesis, 27(7):1445-53 (2006).

Wang et al., Covalent micropatterning of poly(dimethylsiloxane) by photografting through a mask, Anal. Chem., 77(23):7539-46 (2005).

Yang et al., Construction of polyfunctional coatings assisted by gallic acid to facilitate co-immobilization of diverse biomolecules, ACS Appl. Mater. Interfaces, 5(21):10495-501 (2013).

You et al., Gallic acid-induced lung cancer cell death is related to glutathione depletion as well as reactive oxygen species increase, Toxicol. in Vitro, 24(5):1356-62 (2010).

Japanese Patent Application No. 2016-502451, Notice of Reasons for Rejection (English translation), dated Nov. 21, 2017.

* cited by examiner

XPS survey spectra of polysulfone surfaces modified with chitooligosaccharide, gallic acid, and different levels of heparin.

Plot of thrombin conversion (ng/ml)

IMMOBILIZATION OF AN ACTIVE AGENT ON A SUBSTRATE

CROSS-REFERENCE TO RELATED APPLICATION

This application is a divisional of U.S. patent application Ser. No. 14/212,325, filed Mar. 14, 2014, which claims the priority benefit under 35 U.S.C. § 119(e) of U.S. Provisional Application No. 61/798,765, filed Mar. 15, 2013, all of which are expressly incorporated herein by reference and made a part hereof.

NAMES OF PARTIES TO A JOINT RESEARCH AGREEMENT

The claimed invention was made as a result of activities undertaken within the scope of a joint research agreement between Baxter Healthcare Corporation, and Northwestern University.

FIELD OF THE INVENTION

The invention relates generally to the immobilization of an active agent on a substrate. More particularly, the invention relates to methods of immobilizing an active agent on a substrate, substrates with active agents immobilized thereto, and medical devices comprising substrates with active agents immobilized thereto.

BRIEF DESCRIPTION OF RELATED TECHNOLOGY

Medical devices and medical device components that are used for hemodialysis or other applications that involve contact between physiologic fluids, such as blood, or tissue and the medical device or device component are known to become fouled with protein, cell, and/or bacterial deposits from the contact. The deposition of protein from the blood onto medical devices or medical device components is problematic for a number of materials commonly used as substrates for medical devices and medical device components, especially polysulfone, polycarbonate, and silicone. In many cases, the fouling can impair function or lead to failure of the medical device. This problem is particularly significant for extracorporeal blood circuits and components thereof such as the tubing used in a hemodialysis set.

Coating substrates with active agents, for example, antifouling/antimicrobial agents, is known in the art. For example, 3,4-dihydroxyphenylalanine (DOPA) has been used to synthesize dihydroxyphenyl containing polymers which can be used as adhesive polymers which also provide antifouling/antimicrobial coatings, as described in U.S. Pat. No. 7,618,937, and U.S. Patent Application Publication Nos. 2010/0028719, 2009/0123652, 2008/0247984, 2008/0169059, and 2006/0009550. Typically, the polymers derived from DOPA comprise anchor moieties comprised of peptides, such as lysine, copolymerized with DOPA, as shown in structure (I) below, which can be costly to mass produce. It is believed that a peptide or peptoid moiety, coupled to the anchor moiety is generally resistant to, or inhibits protein adsorption or cell fouling of the surfaces onto which the composition is coated or attached.

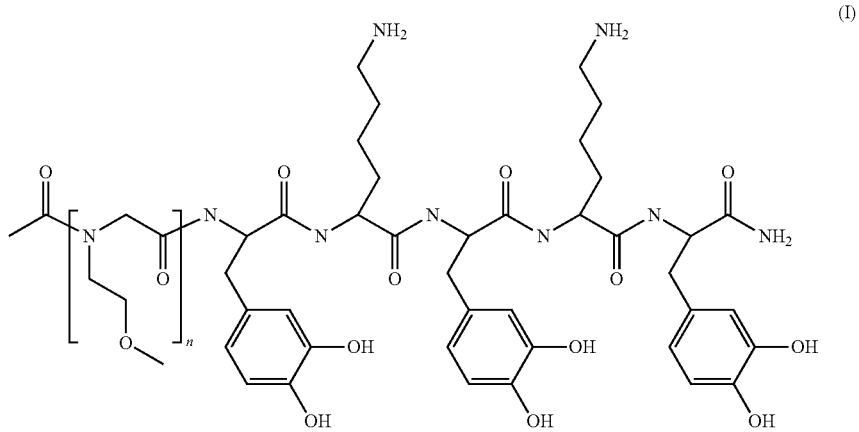

(I)

Alternatively, U.S. Pat. No. 7,622,533 and U.S. Patent Application Publication No. 2010/0197868 describe an adhesive polymer including pendant DOPA groups or dihydroxyphenyl (DHDP) derivatives attached thereto to form adhesive polymers capable of binding to a dissimilar substrate, as shown in structure (II) below.

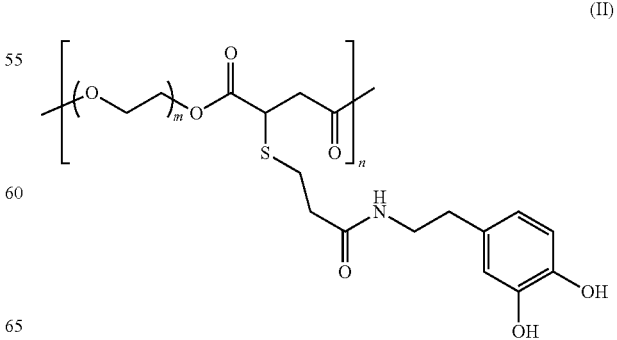

(II)

However, with both approaches, leaching of the DOPA from the polymer is a significant toxicity concern.

SUMMARY

The invention provides methods of immobilizing an active agent on a substrate surface, including the steps of, depositing a primer compound on a substrate thereby forming a primed substrate, contacting the primed substrate with a solution of a compound including a trihydroxyphenyl group, thereby coupling the trihydroxyphenyl group to the substrate to provide a trihydroxyphenyl-treated primed substrate, and contacting the trihydroxyphenyl-treated primed substrate with a solution of an active agent, thereby immobilizing the active agent on the surface thereof. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

In a related aspect, the invention further provides methods of immobilizing an active agent on a substrate, including the steps of depositing a primer compound on a substrate thereby forming a primed substrate, combining in solution a compound including a trihydroxyphenyl group and an active agent, thereby forming a solution of an active agent-trihydroxyphenyl conjugate, and contacting the primed substrate with the solution of the active agent-trihydroxyphenyl conjugate, thereby coupling the trihydroxyphenyl group of the active agent-trihydroxyphenyl conjugate to the primed substrate, and immobilizing the active agent on the surface thereof. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

The invention further provides methods of immobilizing an active agent on a substrate surface, including the steps of, depositing a primer compound on a substrate, thereby forming a primed substrate, contacting the primed substrate with a solution of gallic acid, thereby coupling the gallic acid to the substrate to provide a gallic acid-treated primed substrate, and contacting the gallic acid-treated primed substrate with a solution of an active agent, thereby immobilizing the active agent on the substrate surface.

In another related aspect, the invention provides substrates having an active agent immobilized on a surface thereof, the substrate including a layer of a primer compound on the substrate surface, wherein the layer of the primer compound includes a trihydroxyphenyl group coupled thereto, and wherein the trihydroxyphenyl group includes an active agent coupled thereto and thereby immobilized on the substrate surface. The active agent can be coupled to the trihydroxyphenyl group and/or the primer compound via a linker compound, so as to immobilize the active agent on the substrate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group.

In another related aspect, the invention provides medical devices including a substrate according to the invention.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to specific embodiments described herein.

DETAILED DESCRIPTION

Figure 1:
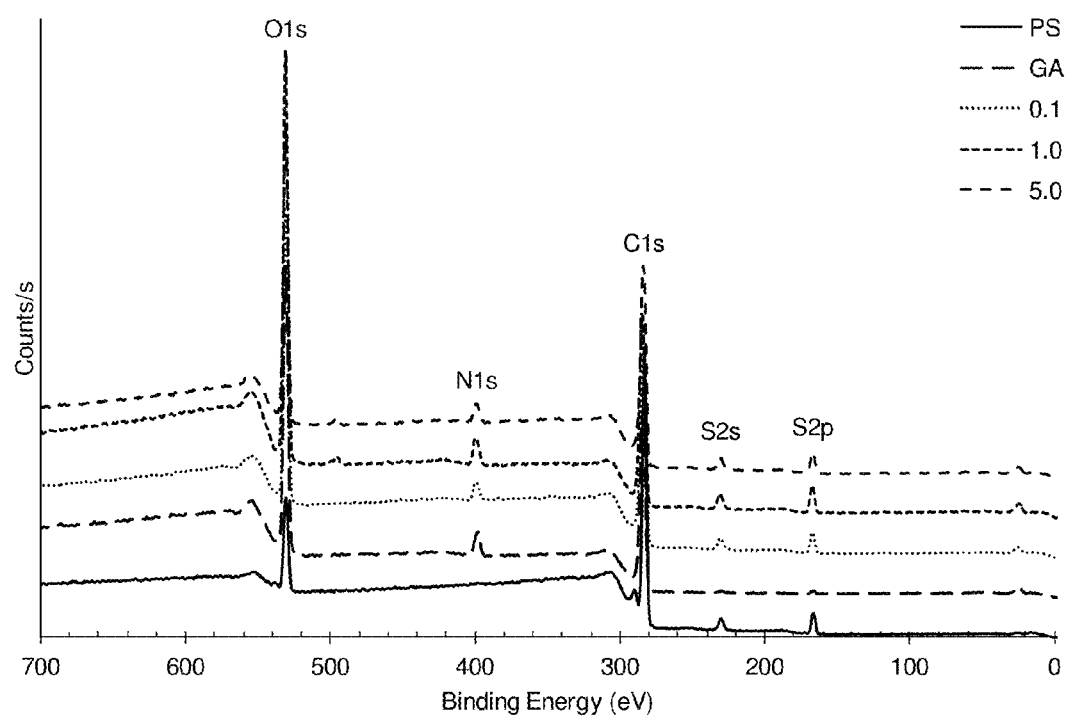
FIG. 1 shows x-ray photoelectron survey spectra of polysulfone surfaces modified with (i) unmodified polysulfone surface, (ii) chitooligosaccharide and gallic acid and (iii) chitooligosaccharide, gallic acid and different concentrations of heparin.

The invention provides substrates with an active agent advantageously and securely immobilized on a surface thereof and methods for forming same. The substrates with an active agent immobilized thereto are particularly advantageous in that they can be produced relatively inexpensively, particularly relative to prior art substrates coated with adhesive polymers derived from peptide-DOPA copolymers. The substrates with active agents immobilized thereto can also be particularly advantageous in that they demonstrate low toxicity, particularly relative to prior art substrates coated using DOPA-based adhesive polymers.

The invention provides methods of immobilizing an active agent on a substrate surface, including the steps of, depositing a primer compound (generally including a nucleophilic group) on a substrate, thereby forming a primed substrate, contacting the primed substrate with a solution of a compound including a trihydroxyphenyl group to couple the compound including a trihydroxyphenyl group to the primer compound, thereby coupling the trihydroxyphenyl group to the substrate to provide a trihydroxyphenyl-treated primed substrate, and contacting the trihydroxyphenyl-treated primed substrate with a solution of an active agent to couple the active agent to the trihydroxyphenyl group, thereby immobilizing the active agent on the surface thereof. The methods can further include the step of contacting the trihydroxyphenyl-treated primed substrate with a solution of a linker compound thereby coupling the linker compound to the trihydroxyphenyl group and/or the primer compound of the trihydroxyphenyl-treated primed substrate, prior to contacting the trihydroxyphenyl-treated substrate with the active agent.

As used herein, "immobilizing" or "immobilized" encompasses any of securing, attaching, affixing, connecting, and/or joining, an active agent to a substrate surface. Immobilization of the active agent to the substrate surface can be confirmed using a number of different techniques. For example, as demonstrated in the examples, the immobilization of the active agent can be confirmed by demonstrating that the activity of the active agent is present using assays known in the art. The activity of the active agent can be assessed with functional assays. For example, a thrombogenic assay can be used to detect anti-thrombogenic agents such as heparin, 4-hydroxycoumarin, and the like. Further, for example, the active agent may be labeled with a fluorescent dye, an isotopic label, or a radiolabel that can be detected on the substrate when the active agent is immobilized thereto. The presence of the active agent can also be determined with surface spectroscopies such as x-ray photoelectron spectroscopy (XPS), Fourier transform infrared reflection-absorption spectroscopy (FTIRRAS), and Raman spectroscopy. Further, cationic stains can be used to confirm/detect the presence of anionic active agents, for example, Alcian blue and Toluidine blue form a complex with anionic active agents such as heparin.

As used herein, "coupling" and "couple" encompass any of covalent bond formation, hydrogen bond formation, ionic bond formation (e.g., electrostatic attraction), and van der Waals interactions, for example, through which the compound including a trihydroxyphenyl group can adsorb to/adhere to/couple to/associate with the primer layer or a linker compound, and through which the active agent can adsorb to/adhere/couple to/associate with a compound including a trihydroxyphenyl group or a linker compound.

As used herein, "compound including a trihydroxyphenyl group" encompasses small molecule compounds, polymers including trihydroxyphenyl groups, and trihydroxyphenyl-linker conjugates. The polymers including trihydroxyphenyl groups include polymers wherein the trihydroxyphenyl group is in the polymer backbone, and polymers including at least one monomer having a pendant trihydroxyphenyl group.

As used herein, "trihydroxyphenyl group" refers to a compound comprising a phenyl ring substituted with at least three hydroxyls. The trihydroxyphenyl group therefore includes compounds comprising a phenyl ring substituted with three hydroxyls, and even with four hydroxyls. Generally, compounds comprising a phenyl ring substituted with at least three hydroxyls are preferred. Compounds comprising a phenyl ring substituted with three hydroxyls are advantageous because in addition to the three hydroxyl groups, such compounds have three potential sites of reactivity available, which sites can be selected from but are not limited to unsubstituted carbons and reactive groups. For example, two unsubstituted carbons and/or reactive groups can couple the compound including a trihydroxyphenyl group to a primer compound and an active agent, a primer compound and a linker compound, or to two additional compounds including a trihydroxyphenyl group via sites of reactivity on the additional trihydroxyphenyl groups (i.e., resulting in polymer formation). A compound with a third site of reactivity, in addition to the coupling that can be done with two sites of reactivity, can advantageously also couple to a linker compound, an active agent, or another compound including a trihydroxyphenyl group, and can be particularly advantageous for crosslinking of polymers including trihydroxyphenyl groups. Further, without intending to be bound by any particular theory, it is believed that compounds comprising a phenyl ring substituted with three hydroxyls are advantageous over compounds having one or two hydroxyls because typically the unsubstituted carbons on compounds comprising three hydroxyls are relatively more reactive. For example, as the number of hydroxyls on the phenyl ring increases, the rate of oxidation generally increases and thus it is typically relatively easier for compounds containing trihydroxyphenyl groups to form quinone-like species than corresponding compounds have phenyl groups substituted with only one or two hydroxyls. Consequently, compounds comprising a phenyl ring substituted with at least three hydroxyls typically have unsubstituted carbons that are relatively more reactive than unsubstituted carbons on corresponding compounds having phenyl groups substituted with only one or two hydroxyls.

As used herein, "sites of reactivity" or "reactive sites" on the compound including a trihydroxyphenyl group do not refer to the hydroxyl moieties themselves, but refer to any other site on the compound including a trihydroxyphenyl group through which an active agent, primer compound, linker compound, or additional compound including a trihydroxyphenyl group can couple to the compound including a trihydroxyphenyl group. For example, sites of reactivity can include unsubstituted carbons and reactive groups which can include, but are not limited to, carboxyls, carboxylates, amides, acyl halides, aldehydes, ketones, and esters Of course, the hydroxyl moieties of the compound including a trihydroxyphenyl group can also demonstrate reactivity, for example, by forming ester linkages with primer compounds having acid side chains such as poly(methacrylic acid), poly(acrylic acid), poly(glutamic acid), and poly(malic acid).

As used herein, "polymer" encompasses any compound with two or more repeat units, for example, dimers, trimers, and higher oligomers. The repeat units can be the same such that a homopolymer is provided, or different such that a copolymer is provided.

As used herein, "active agent" encompasses active agents (including those specifically mentioned herein) and active agent-linker conjugates.

As used herein, "linker compound" encompasses any compound that has at least two end groups such that the linker compound can couple to and thereby connect two separate molecules. For example, the linker compound can couple to either a reactive group and/or an unsubstituted carbon of the trihydroxyphenyl group through a first end group and to a polymerizable moiety through a second end group, so as to form a polymerizable monomer. Alternatively, the linker compound can couple to either a reactive group and/or an unsubstituted carbon of the trihydroxyphenyl group through a first end group and to an active agent through a second end group so as to form a trihydroxyphenyl-linker-active agent conjugate.

In a related aspect, the invention further provides methods of immobilizing an active agent on a substrate, including the steps of depositing a primer compound on a substrate thereby forming a primed substrate, combining in solution a compound including a trihydroxyphenyl group and an active agent to couple the compound including a trihydroxyphenyl group and the active agent, thereby forming a solution of an active agent-trihydroxyphenyl conjugate, and contacting the primed substrate with the solution of the active agent-trihydroxyphenyl conjugate, thereby immobilizing the active agent on the substrate. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group. The active agent-trihydroxyphenyl conjugate can include active agents coupled to linker compounds that are further coupled to trihydroxyphenyl conjugates. The combining and contacting steps can be conducted simultaneously such that the compound including the trihydroxyphenyl group and the active agent are combined in the presence of the primed substrate, or alternatively the combining and contacting steps can be conducted separately and in sequence.

As used herein, "conjugate" refers to the species that result from the coupling together of two or more of a compound including a trihydroxyphenyl group, a linker compound, and/or an active agent. The species that have been conjugated are provided immediately before the term "conjugate." The conjugate can be formed by coupling the two species that are to form a conjugate, as defined above.

In a related aspect, the invention further provides methods of immobilizing an active agent on a substrate surface, including the steps of, depositing a primer compound on a substrate, thereby forming a primed substrate, contacting the primed substrate with a solution of gallic acid to couple the trihydroxyphenyl group of the gallic acid to the primer compound, thereby forming a gallic acid-treated primed substrate, and contacting the gallic acid-treated primed substrate with a solution of an active agent to couple the active agent to the trihydroxyphenyl group of the gallic acid, thereby immobilizing the active agent on the substrate surface. The method can further include the step of contacting the gallic acid-treated primed substrate with a solution of a linker compound thereby coupling the linker compound to the trihydroxyphenyl group and/or the primer compound of the gallic acid-treated primed substrate, prior to contacting the trihydroxyphenyl-treated substrate with the solution of active agent.

In another related aspect, the invention provides substrates having an active agent immobilized on a surface thereof, the substrate including a layer of a primer compound on the substrate surface, wherein the layer of the primer compound includes a trihydroxyphenyl group coupled thereto, and wherein the trihydroxyphenyl group has an active agent coupled thereto and thereby immobilized on the substrate surface. The compound including a trihydroxyphenyl group can be a small molecule or a polymer including a trihydroxyphenyl group. The polymer can be a polymer including the trihydroxyphenyl group in the backbone of the polymer, or alternatively a polymer including at least one monomer having a pendant trihydroxyphenyl group. The active agent can be coupled to the trihydroxyphenyl group and/or the primer compound via a linker compound, so as to immobilize the active agent on the substrate.

In another related aspect, the invention provides medical devices including a substrate according to the invention. Medical devices and medical device components comprising substrates according to the invention can include active agents that advantageously render the device or device component antibacterial, antifouling, and/or anti-thrombogenic. Of course, the active agents can demonstrate other therapeutic or beneficial activities.

The medical devices and medical device components comprising active agents immobilized thereto can be particularly advantageous because the medical device or device component can be effectively "coated" by immobilizing an active agent on/to a (substrate) surface thereof and thereby reduce the need to treat a patient with the (same or similar) active agent. For example, patients whose treatment requires an extracorporeal blood circuit, such as for hemodialysis, apheresis, or coronary bypass, are often administered heparin (or similar acting active agents) prior to the procedure so as to prevent blood clot formation in the blood circuit pumps and tubings. However, in addition to inhibiting clot formation, administration of significant amounts of heparin can render the patient susceptible to bleeding after the treatment. Therefore, it would be advantageous to use blood circuit devices with heparin immobilized thereto, thereby reducing the amount of heparin needed for treatment prior to the procedure and the attendant risk of the patient experiencing bleeding problems and/or needing extended hospitalization or medical care subsequent to the procedure.

In general, the methods according to the invention result in an active agent immobilized on a substrate surface through the use of a compound including a trihydroxyphenyl group that can couple to a primer layer coupled to and/or deposited on the substrate surface. The methods described herein can include the use of solutions and plasmas of primer compounds, solutions of compounds including a trihydroxyphenyl group (e.g., solutions of trihydroxyphenyl-linker conjugates, solutions of small molecule compounds including trihydroxyphenyl groups such as gallic acid, and solutions of polymers including trihydroxyphenyl groups such as polygallic acid), solutions of linker compounds, solutions of active agents (including solutions of active agent-linker conjugates), and solutions of active agent-trihydroxyphenyl conjugates. The solvents used to prepare the solutions of primer compounds, solutions of compounds including a trihydroxyphenyl group, solutions of linker compounds, solutions of active agents, and solutions of active agent-trihydroxyphenyl conjugates can be any solvent suitable to act as a carrier for the primer compounds, compounds comprising a trihydroxyphenyl group, linker compounds, active agents, and/or active agent-trihydroxyphenyl conjugates. For example, the solutions described herein can comprise aqueous solutions, other solvents including but not limited to, alcohols, diols, organosulfurs such as sulfolane, ethers, such as diethyl ether and tetrahydrofuran, alkanes, aromatics, halocarbons, such as chloroform and dichloromethane, and combinations of the foregoing. When the term "solution" is used herein, it is not necessary that the components contained therein completely dissolve. Thus, as used herein, the term solution encompasses both dispersions in which components are dispersed and solutions in which components are substantially or even completely dissolved. In general, complete dissolution of the component is preferred. Further, as used herein, the term "solution" includes aerosolized solutions.

In one aspect of the invention, the method of immobilizing the active agent on the substrate surface, includes the steps of:
(a) contacting a substrate with a primer compound, thereby forming a primed substrate;
(b) contacting the primed substrate with a compound comprising a trihydroxyphenyl group thereby coupling the trihydroxyphenyl group to the primed substrate to provide a trihydroxyphenyl-treated primed substrate; and
(c) contacting the trihydroxyphenyl-treated primed substrate with an active agent to couple the active agent to the trihydroxyphenyl group, thereby immobilizing the active agent on the substrate.

In another aspect of the invention, the method of immobilizing the active agent on the substrate surface, includes the steps of:
(a) contacting a substrate with a primer compound, thereby forming a primed substrate;
(b) contacting the primed substrate with gallic acid to couple the trihydroxyphenyl group of the gallic acid to the primer compound, thereby forming a gallic acid-treated primed substrate; and
(c) contacting the gallic acid-treated substrate with an active agent to couple the active agent to the trihydroxyphenyl group, thereby immobilizing the active agent on the substrate.

In a related aspect, the method of immobilizing an active agent on a substrate surface, includes the steps of:
(a) depositing a primer compound on the substrate thereby forming a primed substrate;

(b) combining in solution a compound including a trihydroxyphenyl group and an active agent to couple the trihydroxyphenyl group and the active agent, thereby forming a solution of an active agent-trihydroxyphenyl conjugate; and (c) contacting the primed substrate with the solution of the active agent-trihydroxyphenyl conjugate, thereby coupling the trihydroxyphenyl group of the active agent-trihydroxyphenyl conjugate to the primed substrate and immobilizing the active agent on the substrate.

In refinements of the aforementioned embodiments, the methods further include washing the primed substrate with water, thereby forming a washed primed substrate, and optionally flowing an inert gas such as nitrogen over the washed primed substrate prior to contacting the washed primed substrate with the solution of a compound including a trihydroxyphenyl group and/or gallic acid solution.

In another refinement of the aforementioned embodiments, the methods further include washing the trihydroxyphenyl- and/or gallic acid-treated primed substrate with water, thereby forming a washed trihydroxyphenyl- and/or gallic acid-treated primed substrate, and optionally flowing an inert gas such as nitrogen over the washed trihydroxyphenyl- and/or gallic acid-treated primed substrate prior to contacting the washed trihydroxyphenyl- and/or gallic acid-treated primed substrate with the solution of active agent.

In yet another refinement of the foregoing embodiments, the methods further include washing the substrate with the active agent immobilized on a surface thereof with water, thereby forming a washed substrate with the active agent immobilized on a surface thereof and optionally flowing an inert gas such as nitrogen over the washed substrate with the active agent immobilized on the surface thereof.

In yet another refinement of the foregoing embodiments, the methods further include the step of contacting the trihydroxyphenyl-treated primed substrate with a solution of a linker compound thereby coupling the linker compound to the trihydroxyphenyl group and/or the primer compound of the trihydroxyphenyl-treated primed substrate, prior to contacting the trihydroxyphenyl-treated substrate with the solution of active agent.

The method can be selected such that the density of the active agent-trihydroxyphenyl conjugates coupled to the substrate can be controlled. Without intending to be limited by any particular theory, it is believed that when the trihydroxyphenyl group is coupled to the primed substrate prior to coupling the active agent to the trihydroxyphenyl group, the resulting trihydroxyphenyl-treated substrate has a relatively dense covering of trihydroxyphenyl groups coupled to the substrate. It is further believed that when an active agent-trihydroxyphenyl conjugate is formed prior to coupling the trihydroxyphenyl group to the primed substrate, the resulting substrate with an active agent immobilized thereto has a relatively lower density of active agent-trihydroxyphenyl conjugates coupled to the surface, when compared to the trihydroxyphenyl-treated substrate prepared prior to coupling the active agent to the trihydroxyphenyl group. When the active agent-trihydroxyphenyl conjugate is formed prior to coupling the trihydroxyphenyl group to the substrate, the conditions can be easily controlled by one of ordinary skill in the art such that the coupling of unsubstituted carbons of the trihydroxyphenyl group to the primed substrate is favored over the coupling of any potential binding sites present on the active agent or reactive groups on the trihydroxyphenyl group to the primed substrate.

Substrates

In general, the substrate to which the active agent is (or will be) immobilized can be any substrate. The surface of the substrate can be hydrophobic or hydrophilic in nature. Suitable substrates can include, but are not limited to, inorganic oxides (e.g., silicas, materials conventionally known as glass), ceramics, metals including metal oxides, semiconductors, and/or polymeric substrates. Metal substrates can include, but are not limited to, stainless steel, cobalt, titanium, nickel, zirconium, tantalum, chromium, tungsten, molybdenum, manganese, iron, vanadium, niobium, hafnium, aluminum, tin, palladium, ruthenium, iridium, rhodium, gold, silver, platinum, oxides of the foregoing, alloys of the foregoing, and combinations of the foregoing. Suitable polymer substrates can include, but are not limited to, acrylonitrile butadiene styrenes, polyacrylonitriles, polyamides, polycarbonates, polyesters, polyetheretherketones, polyetherimides, polyethylenes, polyethylene terephthalates, polylactic acids, polymethyl methacrylates, polypropylenes, polystyrenes, polyurethanes, polyvinyl chloride, polyvinylidene chlorides, polyethers, polysulfones, silicones, polydimethylsiloxanes, polytetrafluoroethylene, polyisoprenes, and blends and copolymers thereof. In one aspect, the substrate has a surface including a suitable reactive moiety ab initio. Substrates of the invention also include those that have surfaces that have been activated (or modified) in order to facilitate the formation of a uniform primer layer. Reactive moieties are useful in that they can be used to covalently bond primer compounds to the substrate surface. Such reactive moieties, however, need not be present as the primer compounds will still adsorb to/adhere to/couple to/associate with the substrate in the absence of reactive moieties on the substrate surface.

The substrate according to the invention can be used to provide one or more surfaces of a medical device or medical device component. The medical device or medical device component can be any medical device or medical device component that may benefit from having an active agent immobilized on the surface thereof, particularly medical devices which are in regular contact with the biological fluids of a patient. Medical devices or medical device components can include but are not limited to instruments, apparatuses, implements, machines, contrivances, implants, and components and accessories thereof, intended for use in the diagnosis, cure, mitigation, treatment, or prevention of disease or other condition in humans or other animals, or intended to affect the structure or any function of the body of humans or other animals. Exemplary medical devices can include, but are not limited to, extracorporeal blood circuit devices such as hemodialysis and coronary bypass pumps and components thereof. Autotransfusion, apheresis, hemofiltration, plasmapheresis, and extracorporeal membrane oxygenation also involve the use of an extracorporeal blood circuit for removing blood from a patient's circulation and applying a process thereto prior to returning the blood to the patient's circulation.

Specific medical devices and/or medical device components that include substrates that benefit from having an active agent immobilized on the surface thereof include, but are not limited to, tubing; fluid bags; septa; stopcocks; clamps; filters; catheters, such as venous catheters, urinary catheters, Foley catheters, intraurethral catheters, intra-arterial catheters, intraosseous catheters, intrathecal catheters, intra-pulmonary catheters and pain management catheters; tracheal tubes; nasogastric tubes; dialysis sets; dialysis connectors; stents; abdominal plugs; feeding tubes; indwelling devices; surgical tools; needles; cannulae; medical pumps; pump housings; gaskets such as silicone O-rings; syringes;

surgical sutures; filtration devices; drug reconstitution devices; implants; metal screws; and metal plates. Additional exemplary medical devices include, but are not limited to, invasive medical devices, durable medical devices, medical fluid containers, medical fluid flow systems, infusion pumps, patient monitors, and any other medical devices which regularly come into contact with a patient's biological fluids.

Examples of durable medical devices include intravenous (I.V.) pumps, patient monitors, and the like. Examples of medical fluid flow systems include I.V. sets, intraperitoneal sets, and components thereof, such as, for example, Luer access devices. A typical I.V. set uses plastic tubing to connect a phlebotomized subject to one or more medical fluid sources, such as intravenous solutions or medicament containers. I.V. sets optionally include one or more access devices providing access to the fluid flow path to allow fluid to be added to or withdrawn from the IV tubing. Access devices advantageously eliminate the need to repeatedly phlebotomize the subject and allow for immediate administration of medication or other fluids to the subject, as is well known. Access devices can be designed for use with connecting apparatus employing standard Luers, and such devices are commonly referred to as "Luer access devices," "Luer-activated devices," or "LADs." LADs can be modified with one or more features such as antiseptic indicating devices. Various LADs are illustrated in U.S. Pat. Nos. 5,242,432, 5,360,413, 5,730,418, 5,782,816, 6,039,302, 6,669,681, and 6,682,509, and U.S. Patent Application Publication Nos. 2003/0141477, 2003/0208165, 2008/0021381, and 2008/0021392, the disclosures of which are hereby incorporated by reference in their entireties.

I.V. sets or intraperitoneal sets can incorporate additional optional components including, for example, septa, stoppers, stopcocks, connectors, protective connector caps, connector closures, adaptors, clamps, extension sets, filters, and the like. Thus, additional suitable medical devices and medical device components which may be benefit from the invention include, but are not limited to: I.V. tubing, I.V. fluid bags, I.V. set access devices, septa, stopcocks, I.V. set connectors, I.V. set connector caps, I.V. set connector closures, I.V. set adaptors, clamps, I.V. filters, I.V. pumps, I.V. poles, catheters, needles, cannulae, stethoscopes, patient monitors, intraperitoneal tubing, intraperitoneal fluid bags, access devices for intraperitoneal sets, intraperitoneal set connectors, intraperitoneal set adaptors, and intraperitoneal filters. Representative access devices include, but are not limited to: Luer access devices including, but not limited to, needleless Luer access devices. The surface of the medical device can be any substrate as described herein.

Primer Compound

Generally, the primer compound can be any compound that when deposited on a substrate forms a layer on the surface of the substrate and allows a trihydroxyphenyl group to couple to the primer. As used herein, the term "primer compound" includes both small molecules and polymers. The trihydroxyphenyl group adsorbs to/adheres to/couples to/associates with the primer compound through covalent bond formation, hydrogen bond formation, ionic bond formation, van der Waals interactions, or combinations of the foregoing. Typically, the compound including a trihydroxyphenyl group is coupled to the primer by forming one or more covalent bonds with the primer. In general, the primer compound is believed to form a "network" with the compounds including a trihydroxyphenyl group. As used herein, the term "network" refers to covalent bonds formed between an unsubstituted carbon of the trihydroxyphenyl group phenyl ring and any two or more compounds selected from a primer compound, a second trihydroxyphenyl group of a compound including a trihydroxyphenyl group (which may be a trihydroxyphenyl group of a small molecule including a trihydroxyphenyl group and/or a polymer including a trihydroxyphenyl group), and/or combinations of the foregoing. In embodiments wherein a relatively high density of primer compounds and/or compounds including a trihydroxyphenyl group are covalently bound, a cross-linked network can be formed. In embodiments wherein there is a relatively low density of primer compounds and/or compounds including a trihydroxyphenyl group covalently bound, the resulting network may not be cross-linked.

Suitable primer compounds include a nucleophilic group. Suitable nucleophilic groups are well known in the art and can include, but are not limited to, hydroxyl, alkoxide, amine, nitrite, thiol, thiolate, imidazole, and combinations thereof. Suitable primer compounds include, but are not limited to, oligosaccharides such as chitooligosaccharide, fructooligosaccharide, galactooligosaccharide, mannanoligosaccharide, polyamines such as ethylenediamine, 1,2-diaminopropane, hexamethylenediamine, tetramethylenediamine, pentamethylenediamine, tetraethylmethylenediamine, spermine, spermidine, and polyethyleneamine, poly(methacrylic acid), poly(acrylic acid), poly(glutamic acid), poly(malic acid), amino functionalized silanes including alkoxyaminosilanes such as aminopropyltriethyoxysilane, aminopropyldiethoxymethylsilane, aminopropyldimethylethoxysilane, and aminopropyltrimethoxysilane, and mercaptosilanes such as mercaptopropyltrimethoxysilane and mercaptopropylmethyldimethoxysilane. Nucleophilic groups on oligosaccharides include amine and hydroxyl groups; nucleophilic groups on polyamines include amine groups. Of course, other nucleophilic groups are possible and the foregoing groups are only provided to illustrate aspects of the invention.

Because the primer compound can be a small molecule or a polymer, the molecular weight of the primer compound can be suitably varied over a large molecular weight range. As described below, the molecular weight of the primer compound is typically chosen such that the primer compound is fully soluble in a chosen solvent (i.e., preferably, without forming a saturated primer compound solution). Alternatively, when a plasma is used to deposit the primer compound on the substrate, the primer compound can be any molecular weight, provided the compound is suitably volatile to be dispersed into the vapor phase.

As described with chitooligosaccharide in the examples below, it is believed that the primer compound (chitooligosaccharide) can bind to the compound including a trihydroxyphenyl group through a nucleophile on the primer compound that covalently binds with an unsubstituted carbon on the phenyl ring of the trihydroxyphenyl group. Other primer compounds necessarily include a similar nucleophilic group as mentioned above and therefore can bind to the compound including a trihydroxyphenyl group in a similar fashion as chitooligosaccharide. The primer compound can bind to the compound including a trihydroxyphenyl group through other mechanisms as well. For example, an amine present on chitooligosaccharide can form a Schiff base with a compound including a trihydroxyphenyl group that comprises a carbonyl moiety, for example, gallic acid. Other primer compounds having an amine as a nucleophilic group can bind to a compound including a trihydroxyphenyl group that comprises a carbonyl moiety in a similar fashion.

In embodiments of the invention, the primer compound can also function as a secondary active agent (such as an antibacterial agent, an antifouling agent, an anti-inflammatory agent, an anti-thrombogenic agent, e.g., an anticoagulation agent, and combinations thereof). For example, oligosaccharides such as chitooligosaccharide can advantageously act as an antibacterial agent in addition to the primary intended function as primer compound. As another example, chitosan that has been functionalized with quaternary amine groups can be used as a primer compound that also advantageously imparts antibacterial properties to the substrate.

In general, the primer compound forms a substantially uniform layer on the substrate surface. As used herein, "uniform" refers to the uniformity of the amount/number density of primer compound on the substrate surface per unit area of the substrate surface. Typically, the term refers to substantially contiguous coverage on the substrate. Substantially contiguous coverage refers to the primer compound being present on at least about 20% to about 100% coverage of the substrate surface, for example, about 30%, about 40%, about 50%, about 60%, about 70%, about 80%, about 90% and/or about 100% coverage of the substrate surface. Substantially contiguous coverage of the primer compound on the substrate advantageously results in substantially regular/controlled spacing of the active agent ultimately immobilized on the substrate. The uniformity of a given primer compound layer can be confirmed using known techniques such as scanning electron microscopy (SEM), atomic force microscopy (AFM), Fourier transform infrared (FTIR) imaging, Raman imaging, ellipsometric imaging, x-ray photoelectron spectroscopy (XPS) combined with depth profiling, and/or static or dynamic secondary ion mass spectrometry (SIMS) imaging combined with depth profiling. In addition, as mentioned above, the primer compound and the compound including a trihydroxyphenyl group can be coupled to the substrate, for example, by forming a network with one another (e.g., the primer compound and the compound including a trihydroxy group can be introduced in sequence or in combination in the presence of a substrate). The uniformity of the network layer can also be confirmed using known techniques such as scanning electron microscopy (SEM), atomic force microscopy (AFM), Fourier transform infrared (FTIR) imaging, Raman imaging, ellipsometric imaging, x-ray photoelectron spectroscopy (XPS) combined with depth profiling, and/or static or dynamic secondary ion mass spectrometry (SIMS) imaging combined with depth profiling.

Ranges may be expressed herein as from "about" or "approximately" one particular value and/or to "about" or "approximately" another particular value. When such a range is expressed, another embodiment according to the invention includes from the one particular value and/or to the other particular value. Similarly, when particular values are expressed as approximations, but use of antecedents such as "about," "at least about," or "less than about," it will be understood that the particular value forms another embodiment.

Without intending to be bound by any particular theory, it is believed that the uniformity of the primer layer that is deposited on the substrate surface depends upon the hydrophobic/hydrophilic nature of both the substrate surface and the primer compound, and the duration of time that the primer layer is exposed to the substrate surface. For example, it is believed that a substantially uniform layer of a hydrophilic primer compound will form more quickly on a hydrophilic surface than on a hydrophobic surface.

A substrate surface can be modified such that the hydrophilic/hydrophobic nature of the substrate is changed prior to exposure of the primer compound to the substrate surface in order to facilitate the formation of a uniform primer layer. Plasma treatments, including but not limited to, argon or corona treatments, chemical treatments, including but not limited to, acid treatments, base treatments, and the like can be used to activate or modify a non-polar, hydrophobic substrate surface to be more polar/hydrophilic. For example, in one embodiment, a surface may be modified to include a hydroxyl group by oxidation of the substrate surface. Suitable methods of oxidizing substrate surfaces are known in the art and can include, for example, treatment of the substrate surface with any oxidation agent, including, but not limited to hydrogen peroxide, inorganic peroxides, permanganates, including the potassium, sodium, ammonium, and calcium salts, osmium tetroxide, and combinations of the foregoing. As another example, polyester substrates can be activated or modified to include a hydroxyl group by treating the substrate with an acid treatment, a base treatment, or an argon plasma. Suitable methods to activate or modify the substrate to include an amine include treating a polyamide substrate with an acid treatment, a base treatment, or an argon plasma. Suitable methods to modify the substrate to include a thiol include treating a polythioester substrate with an acid treatment, a base treatment, or an argon plasma. Plasma treatments can be followed by exposing the plasma treated substrate to a gas to generate reactive moieties. For example, plasmas can be used to generate radicals and then followed to generate reactive moieties by exposure to gases such as oxygen, ammonia, and hydrogen sulfide and thereby generate hydroxyl, amine, and thiol, respectively.

In embodiments of the invention, the primer compound is deposited on the substrate surface by contacting the substrate surface with a solution of primer compound. Deposition methods can include completely immersing the substrate in a solution of primer compound, for example, by dip coating. Alternatively, deposition methods can include spraying or casting a solution of primer compound onto the substrate surface, for example, by spin casting or spraying a solution such as an aerosolized solution. For substrates having an interior lumen, such as tubing, the solution can also be flowed into the lumen to coat the interior thereof. The solvent can be any solvent that is capable of serving as a carrier for the primer compound. For example, most frequently water is used as the solvent, but organic solvents including but not limited to, alcohols, diols, organosulfurs such as sulfolane, ethers, such as diethyl ether and tetrahydrofuran, halocarbons, such as chloroform and dichloromethane, and combinations of the foregoing can be used. Water is generally preferred for smaller and/or charged primer compounds, but conventional organic solvents can be used, especially for polymeric primer compounds. In embodiments of the methods disclosed herein, the solution comprising the primer compound is at a pH in a range of about 7.5 to about 9.5, or about 8 to about 9, or about 8.5. The solution of primer compound may further include a buffer, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more carbonate, phosphate and other known buffer systems for maintaining relatively high pH values can also be used.

The invention further provides methods of immobilizing an active agent to a substrate surface, including the steps of, depositing the primer compound on the substrate by plasma deposition. The term "plasma" as used herein, describes a partially or fully ionized gas composed of ions, electrons, and neutral species. For example, a layer of reactive amine groups can be deposited on the substrate surface using a plasma treatment comprising allylamine generated by the application of radiofrequency under slight to moderate vacuum. In this example, the plasma treatment results in radical species forming on the surface of the substrate that will initiate radical polymerization of the allylamine on the substrate surface. In addition, radicals formed in the vapor phase of the plasma can interact with radicals formed on the substrate surface and couple to the substrate.

Suitable plasmas can be generated from various inert gases and reactive gases, as well as mixtures of inert gases, mixtures of reactive gases, and/or mixtures of inert gases and reactive gases. Plasmas for use in accordance with the present methods can be generated by various known methods, such as by the application of electric and/or magnetic fields. Various types of power sources can be used to generate suitable plasmas for use in the disclosed methods; typical power sources include direct current (DC), radiofrequency (RF), microwave, and laser power sources. A parallel-plate plasma source, for example, uses a RF power source to generate plasma through gas discharge. Another example of an RF power source is an inductive coupling plasma source which uses an inductively coupled RF source to generate plasma. The RF power source can operate at 13.56 MHz or at another suitable frequency readily determined by one of ordinary skill. Microwave power sources include, for example, the electron cyclotron resonance (ECR) source. The microwave frequency can be 2.45 GHz or another suitable frequency readily determined by one of ordinary skill.

Plasmas can be generated at various pressures, and suitable plasma pressures can be readily determined by one of ordinary skill. Plasma can be generated, for example, at atmospheric pressure or under vacuum. Damage to the substrate can be more prevalent at higher pressures compared to lower pressures. Thus, the use of lower pressures can prevent or reduce damage to the substrate, thereby allowing increased exposure times and/or increased power levels to be used. Typical pressures at which plasma can be generated include pressures of about 0.001 Torr to about 760 Torr, for example, about 0.01 Torr to about 100 Torr, about 0.05 Torr to about 50 Torr, and/or about 0.1 Torr to about 10 Torr, but higher and lower pressures also can be used.

In a further embodiment of the invention, the substrate surface can be modified to include a radical as a reactive moiety by UV irradiation and/or heat treatment (for example, at about 40 to about 110 ° C.) of the substrate in the presence of an initiator to create radicals on the surface of the substrate. The initiator can be any initiator known in the art capable of forming a radical when subjected to UV irradiation and/or elevated temperatures, for example, between about 40 and about 110° C. Suitable initiators can include, but are not limited to, benzophenone, peroxides, including but not limited to hydrogen peroxide, benzoyl peroxide, acetyl peroxide, lauryl peroxide, t-butyl peracetate, t-butyl hydroperoxide, and di-t-butyl peroxide, nitrogen dioxide, azobisisobutyronitrile (AIBN), and 2,2-dimethoxy-2-phenylacetophenone (DMPA). A radical generated on the substrate surface can be converted to reactive moieties such as hydroxyl, amine, and thiol by exposure to gases such as oxygen, ammonia, and hydrogen sulfide, respectively.

Once a substrate surface has been modified to include a reactive moiety such as a hydroxyl, the substrate surface can be further modified such that one reactive moiety is replaced with a different reactive moiety. For example, a thiol can be replaced by a hydroxyl, or vice versa.

The primer compound adsorbs to/adheres to/couples to/associates with the substrate surface through covalent bond formation, hydrogen bond formation, ionic bond formation, van der Waals interactions, or combinations of the foregoing; when a reactive moiety is present on the substrate surface, the primer compound advantageously adsorbs to/adheres to/couples to/associates with the reactive moiety. The primer compound is further coupled to a compound including a trihydroxyphenyl group which is further coupled to an active agent (either before or after coupling of the compound including a trihydroxyphenyl group to the substrate) through an unsubstituted carbon on the trihydroxyphenyl group or through a reactive group on the trihydroxyphenyl group, ultimately forming a substrate with an active agent immobilized thereto. The compound including a trihydroxyphenyl group adsorbs to/adheres to/couples to/associates with the active agent through covalent bond formation, hydrogen bond formation, ionic bond formation, van der Waals interactions, or combinations of the foregoing. Typically, the compound including a trihydroxyphenyl group is coupled to the active agent by forming one or more covalent bonds with the active agent.

When the primer compound is deposited on the substrate surface by contacting the substrate surface with a solution of primer compound, the concentration of the primer compound in the solution of primer compound can generally be any concentration. The concentration is typically chosen such that the primer compound is fully soluble in a chosen solvent, without forming a saturated primer compound solution. Another consideration is the duration of time for conducting the deposition is generally less when higher concentrations are used. Exemplary primer compound concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, about 0.05 to about 3 mg/ml, about 0.05 to about 2 mg/ml, and/or about 0.1 to about 1.5 mg/ml, for example, about 0.1 mg/ml, and/or about 1 mg/ml.

The substrate surface can be contacted with and/or immersed in the solution of primer compound for any duration of time suitable to deposit the primer compound on the substrate surface with the desired primer compound density. The rate of the deposition of the primer compound on the substrate can depend, in part, on the concentration of the primer compound in the primer compound solution, the substrate surface to solution volume ratio, the ionic strength of the solution, the pH of the solution, and the temperature. The duration of contact of the substrate with the solution of primer compound can be varied for any suitable time period which ultimately provides a layer on a substrate, for example, from about 10 seconds to about 24 hours when using dip coating. When the duration of contact of the substrate with the solution of primer compound increases above 24 hours (and one of the foregoing exemplary concentrations of the primer compound is used), little difference in the amount of primer compound deposited and the uniformity of the primer layer are expected (relative to a 24 hour exposure time). Without intending to be bound by theory, while it is believed that after 24 hours deposition of the primer compound may continue, it is expected that the amount of primer compound deposited after 24 hours will have little effect on the amount of active agent that is ultimately immobilized on the substrate surface.

In another embodiment, a primer compound, for example, a polyamine is deposited on the substrate surface by a plasma treatment. The substrate surfaces can be exposed to the plasma for various periods of time. The length of plasma exposure can be readily determined by one of ordinary skill and confirmed using the spectroscopic techniques for determining the uniformity of a primer compound layer mentioned above. Further, the length of exposure can vary depending on the reactivity of the plasma. Damage to the substrate can be more prevalent after longer exposure times compared to shorter exposure times. Thus, the use of shorter exposure times can prevent or reduce damage to the substrate, thereby allowing increased pressure and/or increased power levels to be used. Typically, the substrate surface is exposed for about 1 second to about 2 hours, but shorter and longer exposure periods can be used. Generally, the substrate surface is exposed to the plasma for about 5 seconds to about 1 hour, about 10 seconds to about 30 minutes, about 30 seconds to about 20 minutes, and/or about 1 minute to about 10 minutes.

The substrate surfaces can be exposed to the plasma for a continuous period of time. The substrate surfaces also can be exposed to the plasma for intermittent (or "pulsed") periods of time, i.e., the plasma deposition process can comprise exposure of the substrate surface to the plasma for a period of time, followed by a period during which the substrate surface is not exposed to the plasma. Such periods of exposure and non-exposure can be repeated multiple times. Damage to the substrate or substrate coating can be more prevalent after continuous exposure processes compared to pulsed exposure processes. Thus, the use of pulsed exposure processes can prevent or reduce damage to the substrate or substrate coating, thereby allowing increased pressure and/or increased power levels to be used. Increased power levels over pulsed periods may advantageously reduce the amount of time in which the substrates are exposed to the plasma, thereby reducing part cycle time and increasing manufacturing efficiencies.

Compound Including a Trihydroxyphenyl Group

The primed substrate is exposed to a compound including a trihydroxyphenyl group in order to couple the trihydroxyphenyl group to the primed substrate. As previously described, the compound including a trihydroxyphenyl group adheres/couples to/associates with the primer compound through covalent bond formation, hydrogen bond formation, ionic bond formation, van der Waals interactions, or combinations of the foregoing. Typically, the trihydroxyphenyl group is coupled to the primer by forming one or more covalent bonds with the primer. As described above, the compound including a trihydroxyphenyl group encompasses small molecule compounds, polymers including trihydroxyphenyl groups, and trihydroxyphenyl-linker conjugates. The polymers including trihydroxyphenyl groups include polymers wherein the trihydroxyphenyl group is in the polymer backbone as well as polymers including pendant trihydroxyphenyl groups. The trihydroxyphenyl-linker conjugates include small molecule or polymer compounds including a trihydroxyphenyl group coupled to a linker compound.

Generally, suitable trihydroxyphenyl groups have at least two sites of reactivity such that the trihydroxyphenyl group can bind to a reactive moiety presented by/on/within the primer layer, thereby forming a primer compound-trihydroxyphenyl group network, and also to at least one of the active agent, another compound including a trihydroxyphenyl group, a linker compound, and/or combinations of the foregoing. Suitable small molecule compounds including a trihydroxyphenyl group include, but are not limited to, gallic acid, phloroglucinol, carboxylic acid, gallamide, 5-methylbenzene-1,2,3-triol, 3,4,5-trihydroxybenzaldehyde, 2,3,4-trihydroxybenzaldehyde, gallacetophenone, 3,4,5-trihydroxybenzamide, 2,3,4-trihydroxybenzoic acid, 5-hydroxydopamine hydrochloride, methyl gallate, pyrogallol, derivatives thereof and salts of the foregoing. The aforementioned small molecule compounds can also be used to prepare polymers comprising trihydroxyphenyl groups. Gallic acid, through at least the two unsubstituted carbons on its trihydroxyphenyl group phenyl ring is able to bind to two of a primer compound, an active agent, another gallic acid, a linker compound, and combinations of the foregoing, thereby immobilizing the active agent on the substrate surface. Gallic acid is also able to bind to a primer compound, an active agent, another gallic acid, or a linker compound via its carboxylic acid moiety, as described below for a linker compound. Thus, gallic acid advantageously has three hydroxyls as well as three sites of reactivity that may participate in and facilitate the immobilization of an active agent on the substrate surface. Other compounds including a trihydroxyphenyl group necessarily include at least two sites of reactivity, for example, at least two unsubstituted carbons on the phenyl ring and/or reactive groups (such as the aforementioned carboxylic acid moiety) in order to also be able to couple to two of a primer compound, an active agent, another compound including a trihydroxyphenyl group, a linker compound, and combinations of the foregoing, thereby immobilizing an active agent on the substrate surface. Suitable reactive groups on the phenyl ring of the trihydroxyphenyl group include, but are not limited to, carboxyls, carboxylates, amides, acyl halides, aldehydes, ketones, and esters.

Linker Compounds

The compound including a trihydroxyphenyl group can be coupled to a linker compound thereby forming a trihydroxyphenyl-linker conjugate. The compound including a trihydroxyphenyl group adsorbs to/adheres to/couples to/associates with the linker compound through covalent bond formation, hydrogen bond formation, ionic bond formation, van der Waals interactions, or combinations of the foregoing. Typically, the trihydroxyphenyl group is coupled to the linker compound by forming a covalent bond with the linker compound through an unsubstituted carbon on the trihydroxyphenyl group or through a reactive group on the trihydroxyphenyl group. The reactive group on the trihydroxyphenyl group can be any reactive group that can react with a nucleophile on a linker compound. Suitable reactive groups on the trihydroxyphenyl group include, but are not limited to, carboxyls, carboxylates, amides, acyl halides, aldehydes, and esters. The reactive group on the trihydroxyphenyl group can couple to the linker compound, for example, by transesterification or transamidification. The transesterification or transamidification can optionally be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt). Of course, like the linker compound, an active agent including a nucleophilic group can also couple to the reactive group of the trihydroxyphenyl group by transesterification or transamidification.

The linker compound can be any suitable compound that has a first end group and a second end group that enables the linker to couple to either a reactive group and/or an unsubstituted carbon of the trihydroxyphenyl group and to a polymerizable moiety, so as to form a polymerizable monomer, or to couple to either a reactive group and/or an unsubstituted carbon of the trihydroxyphenyl group and to an active agent so as to form a trihydroxyphenyl-linker-active agent conjugate. Polyethylene glycols, diamines, diols, and dithiols are all useful representative linker compounds. In one aspect, suitable linker compounds include, but are not limited to, compounds according to formula (I):

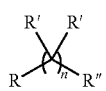

(I)

wherein n is an integer of at least 1, R is any nucleophilic group, including but not limited to hydroxyl, alkoxide, amine, nitrite, thiol, thiolate, imidazole, and amino oxy, R'' is R or a reactive group including, but not limited to, carboxyls, carboxylates, amides, acyl halides, aldehydes and esters, and wherein each R' is the same or different and can be selected from the group consisting of H and substituted or unsubstituted lower alkyl, for example C1 to about C5 alkyl. When aqueous solutions are used, n is typically about 1 to 5 (as long as solubility is achieved in the selected aqueous systems); when organic solvents are used, n can be about 1 to 10. For example, suitable linker compounds can include, but are not limited to, linear bis-amines comprising first and second amine end groups, such as 1,3-diaminopropane, 1,4-diaminobutane, 1,5-diaminopentane, and/or 1,6-diaminohexane.

Suitable linker compounds further include any compound that has two or more terminal functional groups that can couple to either a reactive group and/or an unsubstituted carbon of the trihydroxyphenyl group, a polymerizable moiety, and/or an active agent. As used herein, "terminal" refers to the final functional group of any carbon chain or branch, including, the end groups of linear compounds as well as any branch ends of branched compounds. Typically, the functional groups will be nucleophiles. Nucleophilic groups are well known in the art and can include, but are not limited to, hydroxyl, alkoxide, amine, nitrite, thiol, thiolate, imidazole, aminooxy, and combinations thereof. For example, suitable linker compounds can include, but are not limited branched polyethylene glycol molecules wherein each branch is terminated with a nucleophilic group (including, but not limited to, 8-Arm PEG-aminooxy, 8-Arm PEG-thiol, 8-Arm PEG-amine, 8-Arm PEG-hydroxyl, 4-Arm PEG-aminooxy, 4-Arm PEG-thiol, 4-Arm PEG-amine, 4-Arm PEG-hydroxyl, and the like), dithiols, bisamines, and other polynucleophiles.

It is believed that, upon contacting in solution a compound including a trihydroxyphenyl group and a linker compound, any reactive group(s) and/or unsubstituted carbons on the trihydroxyphenyl group can couple to the linker compound thereby forming a trihydroxyphenyl-linker conjugate. The linker compound adsorbs to/adheres to/couples to/associates with the trihydroxyphenyl group through covalent bond formation, hydrogen bond formation, ionic bond formation, van der Waals interactions, or combinations of the foregoing. Typically, the linker compound is coupled to the trihydroxyphenyl group by forming one or more covalent bonds with the trihydroxyphenyl group. Generic trihydroxyphenyl-linker conjugates can be represented by formula (IIa), (IIb), and (IIc):

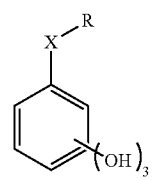

(IIa)

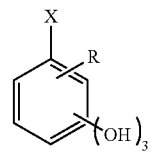

(IIb)

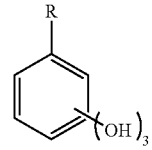

(IIc)

wherein X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (IIa), (IIb), and (IIc) the three hydroxyl groups can be provided on any three of $C_2$, $C_3$, $C_4$, $C_5$, and $C_6$. For example, when the compound including a trihydroxyphenyl group is carboxylic acid such as gallic acid (and thus X is carboxyl), the trihydroxyphenyl-linker conjugate can be of formula (IIa) or formula (IIb):

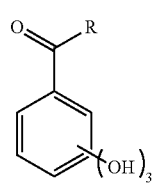

(IIa)

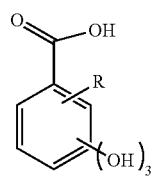

(IIb)

wherein, as above, R is the linker compound. Further, when the trihydroxyphenyl-linker conjugate is a gallic acid-linker conjugate according to (IIa) and (IIb), the three hydroxyl groups are provided on $C_3$, $C_4$, and $C_5$, and the linker, R, is provided on the carboxyl group (IIa) or one of $C_2$ or $C_6$ (IIb). When the compound including a trihydroxyphenyl group is pyrogallol, the pyrogallol-linker conjugate can be of formula (IIc):

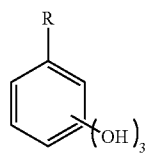

(IIc)

wherein R is the linker compound and the three hydroxyl groups can be provided on any consecutive three of $C_2$, $C_3$, $C_4$, $C_5$, and $C_6$.

The linker compound can be coupled to a compound including a trihydroxyphenyl group prior to contacting a primed substrate with the compound including a trihydroxyphenyl group. Alternatively, a trihydroxyphenyl-treated primed substrate may be contacted with a solution of linker compound, thereby coupling the linker compound to the trihydroxyphenyl group. The linker compound can also couple to the primer compound (which is already coupled to the compound including a trihydroxyphenyl group), for example, by coupling to the reducing end of an oligosaccharide. The linker end group that is distal from the trihydroxyphenyl group can couple to an active agent, thereby forming a trihydroxyphenyl-linker-active agent conjugate, or to a polymerizable moiety, so as to form a polymerizable monomer.

Polymerizable Monomers/Polymers Having Pendant Trihydroxyphenyl Groups

In embodiments wherein the compound including a trihydroxyphenyl group is a polymer, the polymer can include at least one monomer having a pendant trihydroxyphenyl group. A polymer having a pendant trihydroxyphenyl group can be polymerized from polymerizable monomers prepared from a small molecule compound including a trihydroxyphenyl group that has been modified to include a linker compound that includes a polymerizable moiety.

The polymerizable monomer can be formed by coupling a polymerizable moiety to a trihydroxyphenyl-linker conjugate. The trihydroxyphenyl-linker conjugate includes a linker end group distal from the trihydroxyphenyl group. The distal end group of the linker can form a covalent bond with a polymerizable moiety.

In general, the polymerizable moiety can be any functional group that includes a polymerizable α,β unsaturated end group. Suitable polymerizable moieties include, but are not limited to, acrylate, methacrylate, acrylamide, methacrylamide, vinyl acetate, and esters of the foregoing. The covalent bond between the linker compound and the polymerizable moiety may be formed by transesterification or transamidification and may be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt).

In some embodiments, a polymerizable monomer including a trihydroxyphenyl group can also be formed by coupling a reactive group and/or unsubstituted carbon of the phenyl ring of the trihydroxyphenyl group with a linker compound having a first end group and a second end group, wherein the first end group is a nucleophilic group and the second end group is a polymerizable α,β unsaturated end group. Suitable linker compounds of this embodiment include, but are not limited to, 2-hydroxyethyl acrylate, 2-hydroxyethyl methacrylate, 3-hydroxypropyl acrylate, 3-hydroxypropyl methacrylate, 4-hydroxybutyl acrylate, 4-hydroxybutyl methacrylate, 6-hydroxyhexyl acrylate, 6-hydroxyhexyl methacrylate, N-(3-hydroxy-propyl)methacrylamide, N-(4-hydroxybutyl)acrylamide, N-(4-hydroxybutyl)methacrylamide, N-(6-hydroxyhexyl)-acrylamide, N-(6-hydroxyhexyl)methacrylamide, N-methyl-N-(2-hydroxyethyl)acrylamide, N-methyl-N-(2-hydroxyethyl)methacrylamide, N-methyl-N-(3-hydroxypropyl)acrylamide, N-methyl-N-(3-hydroxypropyl)methacrylamide, N-methyl-N-(4-hydroxybutyl)acrylamide, N-methyl-N-(4-hydroxybutyl)methacrylamide, N-methyl-N-(6-hydroxyhexyl)acrylamide, N-methyl-N-(6-hydroxyhexyl)methacrylamide, and 4-aminobutylacrylamide. Generally, suitable linker compounds of this embodiment can include, but are not limited to, compounds according to formula (III):

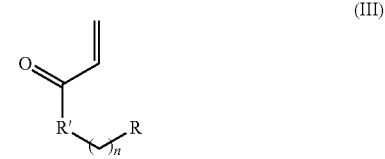

(III)

wherein n is 0 or an integer of at least 1, R is any nucleophilic group, including but not limited to hydroxyl, alkoxide, amine, nitrite, thiol, and thiolate, and R' can be selected from the group consisting of oxygen, NR", and $CR_2"$, and each R" can be the same or different and can be selected from the group consisting of H, and substituted or unsubstituted lower alkyl, for example C1 to about C5 alkyl.

Generic polymerizable monomers including a trihydroxyphenyl group are represented by formula (IVa), (IVb), and (VIc):

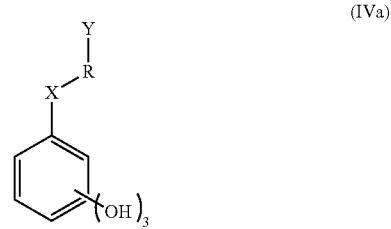

(IVa)

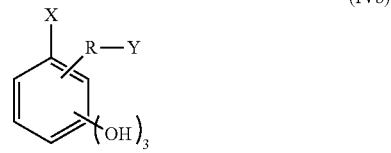

(IVb)

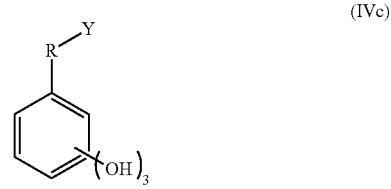

(IVc)

X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate, Y can be a polymerizable moiety such as acrylate, methacrylate, acrylamide, methacrylamide, vinyl acetate, and esters of the foregoing, and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (IVa), (IVb), and (IVc) the three hydroxyl groups can be provided on any three of $C_2$, $C_3$, $C_4$, $C_5$, and $C_6$. For example, when the compound including a trihydroxyphenyl group is a carboxylic acid such as gallic acid (and thus X is carboxyl), the polymerizable monomer including a trihydroxyphenyl group can be of formula (IIa) or formula (IIb):

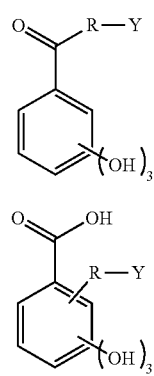

(IVa)

(IVb)

wherein R is the linker compound, and Y is the polymerizable moiety. Further, when the compound including a trihydroxyphenyl group is gallic acid, the polymerizable monomer according to (IVa) and (IVb) comprises the three hydroxyl groups on $C_3$, $C_4$, and $C_5$, and the linker, R, is provided on the carboxyl group (IVa) or one of $C_2$ or $C_6$ (IVb). When the compound including a trihydroxyphenyl group is pyrogallol, the polymerizable monomer can be of formula (IVc):

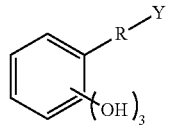

(IVc)

wherein R is the linker compound, Y is the polymerizable moiety, and the three hydroxyl groups can be provided on any consecutive three of C2, C3, C4, C5, and C6.

The polymerizable monomer including a trihydroxyphenyl group is polymerized to form a homopolymer or is copolymerized with one or more secondary polymerizable monomers (including polymerizable groups) to form a polymer containing at least one monomer having pendant trihydroxyphenyl group. Copolymers containing pendant trihydroxyphenyl groups and one or more secondary polymerizable monomers can be polymerized to form random copolymers and/or block copolymers, as is known in the art. Suitable secondary polymerizable monomers can be any monomer comprising a polymerizable moiety. Secondary polymerizable monomers may alternatively have a pendant reactive group (i.e., a reactive group that will be pendant from the monomer after polymerization), including but not limited to N-hydroxysuccinimide, succinimide, and the like, such that when the secondary monomer is incorporated into the polymer containing at least one monomer having a pendant trihydroxyphenyl group the pendant reactive group can couple to the active agent, thereby forming an active agent-trihydroxyphenyl conjugate, or the pendant reactive group can couple to the substrate, thereby forming a trihydroxyphenyl-treated substrate.

Suitable radical initiators for initiating polymerization of the polymerizable monomer having the trihydroxyphenyl group, and optionally a secondary monomer, include, but are not limited to, azo compounds, organic peroxides, and combinations thereof. Suitable azo compounds include, but are not limited to, azobisisobutyronitrile (AIBN), and 1,1-azobis(cyclohexanecarbonitrile) (ABCN). Suitable organic peroxides include, but are not limited to, cyclic peroxides, diacyl peroxides, dialkyl peroxides, hydroperoxides, peroxycarbonates, peroxydicarbonates, peroxyesters, and peroxyketals. Suitable cyclic peroxides include, but are not limited to, 3,6,9-triethyl-3,6,9-trimethyl-1,4,7-triperoxonane. Suitable diacyl peroxides include, but are not limited to, di(3,5,5-trimethylhexanoyl) peroxide. Suitable dialkyl peroxides include, but are not limited to, 2,5-dimethyl-2,5-di(tert-butylperoxy)hexane; 2,5-dimethyl-2,5-di(tert-butylperoxy)hexyne-3; di-tert-amyl peroxide; di-tert-butyl peroxide; and tert-butyl cumyl peroxide. Suitable hydroperoxides include, but are not limited to, tert-Amyl hydroperoxide; and 1,1,3,3-tetramethylbutyl hydroperoxide. Suitable peroxycarbonates include, but are not limited to, tert-butylperoxy 2-ethylhexyl carbonate; tert-amylperoxy 2-ethylhexyl carbonate; and tert-butylperoxy isopropyl carbonate. Suitable peroxydicarbonates include, but are not limited to, di(2-ethylhexyl) peroxydicarbonates; and di-sec-butyl peroxydicarbonates. Suitable peroxyesters include, but are not limited to, tert-amyl peroxy-2-ethylhexanoate; tert-amyl peroxyneodecanoate; tert-amyl peroxypivalate; tert-amyl peroxybenzoate; tert-amyl peroxyacetate; 2,5-dimethyl-2,5-di(2-ethylhexanoylperoxy)hexane; tert-butyl peroxy-2-ethylhexanoate; tert-butyl peroxyneodecanoate; tert-butyl peroxyneoheptanoate; tert-butyl peroxypivalate tert-butyl, peroxydiethylacetate; tert-butyl peroxyisobutyrate; 1,1,3,3-tetramethylbutyl peroxy-2-ethylhexanoate; 1,1,3,3-tetramethylbutyl peroxyneodecanoate; 1,1,3,3-tetramethylbutyl peroxypivalate; tert-butyl peroxy-3,5,5-trimethylhexanoate; cumyl peroxyneodecanoate; tert-butyl peroxybenzoate; and tert-butyl peroxyacetate. Suitable peroxyketals include, but are not limited to, 1,1-di(tert-amylperoxy)cyclohexane; 1,1-di(tert-butylperoxy)cyclohexane; 1,1-di(tert-butylperoxy)-3,3,5-trimethylcyclohexane; and 2,2-di(tert-butylperoxy)butane.

The optional secondary monomer can be included in a copolymer with the monomer having the trihydroxyphenyl group in an amount of up to about 95 mol %, for example, about 0.5 to about 95 mol %, about 0.5 to about 90 mol %, about 1 to about 90 mol %, about 1 to about 85 mol %, about 5 to about 85 mol %, about 5 to about 80 mol %, about 10 to about 80 mol %, about 10 to about 75 mol %, about 15 to about 75 mol %, about 5 to about 70 mol %, about 10 to about 70 mol %, about 15 to about 70 mol %, about 15 to about 65 mol %, about 20 to about 65 mol %, about 20 to about 60 mol %, about 25 to about 60 mol %, about 25 to about 55 mol %, about 30 to about 55 mol %, about 30 to about 50 mol %, about 35 to about 50 mol %, about 35 to about 45 mol %, and/or about 35 to about 40 mol %.

Polymers containing a pendant trihydroxyphenyl group, can be terminated with a reactive group through which an active agent can couple to the polymer. The reactive group can be any reactive group as previously described herein, including, but not limited to, carboxyls, carboxylates, amides, acyl halides, aldehydes, and esters. The reactive group can be included in a compound that can act as a chain transfer agent in polymerizations. Suitable chain transfer agents with reactive groups can include, but are not limited to 3-mercaptopropionic acid, isooctyl 3-mercaptopropionate, and combinations of the foregoing. Alternatively, the active agent will couple to the polymer through an unsubstituted carbon on the pendent trihydroxyphenyl groups and, therefore, the chain end of the polymer need not be able to couple to the active agent.

As described above, compounds including a trihydroxyphenyl group that are polymers containing at least one monomer having a pendant trihydroxyphenyl group can be coupled to a further linker compound, thereby forming a trihydroxyphenyl-linker conjugate that can couple to an active agent. The linker compound adsorbs to/adheres to/couples to/associates with the trihydroxyphenyl group through covalent bond formation, hydrogen bond formation, ionic bond formation, van der Waals interactions, or combinations of the foregoing. Typically, the linker compound is coupled to the trihydroxyphenyl group by forming one or more covalent bonds with the unsubstituted carbons of the trihydroxyphenyl group.

Polymers Having Trihydroxyphenyl Groups in the Backbone

In alternative embodiments wherein the compound including a trihydroxyphenyl group is a polymer, the trihydroxyphenyl group can be in the backbone of the polymer. A polymer having the trihydroxyphenyl groups in the backbone can be polymerized from a small molecule compound including a trihydroxyphenyl group that has at least two sites of reactivity. Without intending to be bound by any particular theory, it is believed that, the small molecule compounds including a trihydroxyphenyl group can self polymerize from a quinone-like species, shown below, by the formation of covalent bonds between unsubstituted carbon atoms in the phenyl rings of two or more adjacent trihydroxyphenyl groups.

The trihydroxyphenyl groups of the compounds including a trihydroxyphenyl group of the invention are generally considered to be in a pH dependent equilibrium with a quinone-like species when in solution. For example, the equilibrium between gallic acid (Compound A) and the quinone-like species (Compound B) is shown below. It is believed that the equilibrium favors the trihydroxylated species, Compound A, at a more acidic pH.

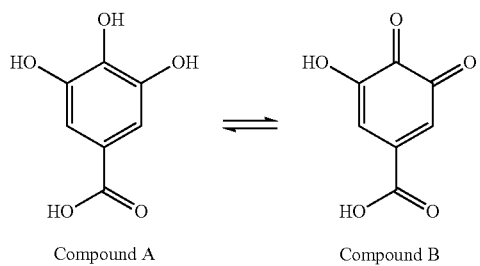 [SMILES: O=C(O)c1cc(O)c(O)c(O)c1 ; O=C(O)C1=CC(=O)C(=O)C(O)=C1]

Compound A    Compound B

After the compound including a trihydroxyphenyl group has come into contact with the primer layer, the trihydroxyphenyl group can covalently bind to a reactive moiety presented by/on/within the layer of primer compound through an unsubstituted carbon of the phenyl ring of the trihydroxyphenyl group, thereby forming a trihydroxyphenyl-treated substrate.

The small molecule compound including a trihydroxyphenyl group can also self polymerize in situ to form polymers containing repeat units of the trihydroxyphenyl group in the polymer backbone. Without intending to be bound by any particular theory, it is believed that the trihydroxyphenyl group can self polymerize from the quinone-like species by the formation of covalent bonds between unsubstituted carbon atoms in the phenyl rings of two or more adjacent trihydroxyphenyl groups. Thus, in one embodiment, the unsubstituted carbon of the phenyl ring to which an active agent can couple can be the terminal trihydroxyphenyl group of a polymer chain that is coupled to the substrate surface.

Further, when the compound including a trihydroxyphenyl group is a polymer including pendant trihydroxyphenyl groups, it is believed that the unsubstituted carbons of the phenyl rings of the pendant trihydroxyphenyl groups can internally cross-link if in close proximity with other pendant trihydroxyphenyl groups on the polymer chain or can crosslink multiple polymer chains.

Further still, it is believed that, upon exposure of the trihydroxyphenyl treated primed substrate to a solution of active agent, any open binding sites on the trihydroxyphenyl group, or linker compounds thereon, can couple to the active agent, thereby immobilizing the active agent on the substrate surface. The active agent adsorbs to adheres to/couples to/associates with the trihydroxyphenyl group through covalent bond formation, hydrogen bond formation, ionic bond formation, van der Waals interactions, or combinations of the foregoing. Typically, the active agent is coupled to the trihydroxyphenyl group (which is already coupled to the layer of primer compound) by forming one or more covalent bonds with the trihydroxyphenyl group. It is believed that the trihydroxyphenyl group can covalently bind with a reactive group of the active agent through an unsubstituted carbon atom of the phenyl ring of the trihydroxyphenyl group. Further, it is believed that, when the reactive group of the active agent is a nucleophile, the covalent bond between the unsubstituted carbon of the phenyl ring of the trihydroxyphenyl group and the reactive group of the active agent may be formed by Michael addition. As exemplified with heparin below, the active agent binds to the trihydroxyphenyl group through a nucleophile on the active agent that covalently binds with an unsubstituted carbon on the phenyl ring of the trihydroxyphenyl group. Other active agents necessarily include a similar nucleophilic group as described below and therefore will bind to the trihydroxyphenyl group in a similar fashion as heparin.

The active agent adsorbs to/adheres to/couples to/associates with a linker coupled to the trihydroxyphenyl group through covalent bond formation, hydrogen bond formation, ionic bond formation, van der Waals interactions, or combinations of the foregoing. Typically, the active agent is coupled to the linker that is coupled to a trihydroxyphenyl group (which is already coupled to the layer of primer compound) by forming one or more covalent bonds with the reactive end group. When the reactive group of the linker compound that will couple to the active agent is a reactive group including, but not limited to, carboxyls, carboxylates, amides, acyl halides, aldehydes and esters, it is believed that the linker is coupled to the active agent through the reactive group on the linker and a nucleophilic group on the active agent. It is further believed that when the reactive group of the linker that will couple to the active agent is a nucleophile, the linker can couple to a reducing end of an active agent, including but not limited to heparin, chitosan, quaternary chitosan, etc., through a residual reactive group on the linker compound.

Coupling of a Compound Including a Trihydroxyphenyl Group and a Primed Substrate.

In one embodiment of the invention, the compound including a trihydroxyphenyl group is coupled to a primed substrate surface by contacting the primed substrate surface with a solution of a compound including a trihydroxyphenyl group. The primed substrate can be completely immersed in the solution of the compound including a trihydroxyphenyl group, for example, by dip coating. Alternatively, a solution of the compound including a trihydroxyphenyl group can be sprayed or cast onto the primed substrate, for example, by spin casting or spraying a solution such as an aerosolized solution. For substrates having an interior lumen, such as tubing, the solution can be flowed into the lumen to coat the interior thereof. The solvent can be any solvent that is capable of serving as a carrier for the compound including a trihydroxyphenyl group. For example, most frequently water is used, but other solvents including but not limited to, alcohols, diols, ethers, such as diethyl ether and tetrahydrofuran, halocarbons, such as chloroform and dichloromethane, and combinations of the foregoing can be used. In embodiments of the methods disclosed herein, the solution comprising the compound including a trihydroxyphenyl group is at a pH in a range of about 7.5 to about 9.5, about 8 to about 9, and/or about 8.5 so the equilibrium is not biased toward either direction of the equilibrium as mentioned above. The solution of the compound including a trihydroxyphenyl group may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), N-tris (hydroxymethyl)methylglycine (Tricine), and combinations thereof. Of course, one or more of citrate, carbonate, lactate, phosphate and other known buffer systems can also be used. Of course, one or more of carbonate, phosphate and other known buffer systems for maintaining relatively high pH values can also be used.

The concentration of the compound including a trihydroxyphenyl group in the solution thereof can generally be any concentration. The concentration is typically chosen such that the compound including a trihydroxyphenyl group is fully soluble in a chosen solvent, without forming a saturated solution of the compound including a trihydroxyphenyl group. Further, because the compound including a trihydroxyphenyl group can self-polymerize in situ, the concentration of the compound including a trihydroxyphenyl group is typically selected such that the compound including a trihydroxyphenyl group will be coupled to the primed substrate at an acceptable rate, desirably without excessive self-polymerization or cross-linking, and, therefore, gelling of the solution. Exemplary concentrations of compounds including a trihydroxyphenyl group in solution can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, and/or about 0.05 to about 5 mg/ml, for example, about 1 mg/ml, and/or about 5 mg/ml.

The primed substrate can be contacted with and/or immersed in the solution of the compound including a trihydroxyphenyl group for any duration of time suitable for coupling the compound including a trihydroxyphenyl group to the primed substrate. In embodiments of the invention the duration can be any duration of time suitable for forming a network of the primer compound and the compound including a trihydroxyphenyl group. The rate of the deposition of the compound including a trihydroxyphenyl group on the primed substrate can depend, in part, on the concentration of the compound including a trihydroxyphenyl group in the solution thereof, the substrate surface to solution volume ratio, the ionic strength of the solution, the pH of the solution, and the temperature. The duration of contact of the primed substrate with the solution of compound including a trihydroxyphenyl group can be varied for any suitable time period for coupling the compound including a trihydroxyphenyl group to the primed substrate, for example, when using dip coating, from about 10 seconds to about 24 hours. When the duration of contact of the primed substrate with the solution of the compound including a trihydroxyphenyl group increases above 24 hours (and one of the foregoing exemplary concentrations of the compound including a trihydroxyphenyl group is used), little difference in the amount of compound including a trihydroxyphenyl group reacted with the primer compound is expected (relative to a 24 hour exposure time). Without intending to be bound by theory, while it is believed that after 24-hours the compound including a trihydroxyphenyl group may continue to be coupled to the primed substrate, it is expected that the amount of the compound including a trihydroxyphenyl group provided after 24 hours will have little effect on the amount of active agent that is ultimately immobilized on the substrate surface, and further, it is believed that the likelihood of the compound including a trihydroxyphenyl group self-polymerizing in solution, even at low concentrations, increases with time.

In embodiments of the invention where the compound including a trihydroxyphenyl group comprises a trihydroxyphenyl-linker conjugate, a trihydroxyphenyl-linker conjugate is initially formed by coupling the trihydroxyphenyl group of a small molecule or polymer compound including a trihydroxyphenyl group with a nucleophile on a linker compound via an unsubstituted carbon or reactive group on the phenyl ring of the trihydroxyphenyl group, and is typically followed by contacting the substrate with a solution of the trihydroxyphenyl-linker conjugate. The trihydroxyphenyl-linker conjugate can be formed by combining in solution a compound including a trihydroxyphenyl group and a linker compound. The solution of the compound including a trihydroxyphenyl group and/or the linker compound can be prepared in any solvent capable of acting as a carrier for the compound including a trihydroxyphenyl group and/or the linker compound. For example, most frequently water is used, but other solvents including but not limited to, alcohols, diols, organosulfurs such as sulfolane, ethers, such as diethyl ether and tetrahydrofuran, alkanes, aromatics, halocarbons, such as chloroform and dichloromethane, and combinations of the foregoing can also be used.

In refinements of the aforementioned embodiment, the solutions of compounds including a trihydroxyphenyl group and linker compounds are at a pH in a range of about 7.5 to about 9.5, or about 8 to about 9, or about 8.5. The solution of compound including a trihydroxyphenyl group and/or solution of linker compound may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of carbonate, phosphate and other known buffer systems can also be used.

The concentrations of the compound including a trihydroxyphenyl group and linker compound in solution can be any concentration. The concentrations are typically chosen such that the compound including a trihydroxyphenyl group and/or linker compound are fully soluble in a chosen solvent, without forming saturated solutions. Exemplary compound including a trihydroxyphenyl group and/or linker compound concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of compound including a trihydroxyphenyl group to linker compound can be in a range of about 1:8 to about 8:1, about 1:7 to about 7:1, about 1:6 to about 6:1, about 1:5 to about 5:1, about 1:4 to about 4:1, about 1:3 to about 3:1, and/or about 1:2 to about 2:1, for example about 1:1.

The trihydroxyphenyl-linker conjugate can be coupled to the primed substrate by contacting the primed substrate with a solution of trihydroxyphenyl-linker conjugate. The primed substrate can be completely immersed in the solution of the trihydroxyphenyl-linker conjugate, for example, by dip coating. Alternatively, a solution of the trihydroxyphenyl-linker conjugate can be sprayed or cast onto the primed substrate, for example, by spin casting or spraying a solution such as an aerosolized solution. For substrates having an interior lumen, such as tubing, the solution can be flowed into the lumen to coat the interior thereof.

The concentration of the trihydroxyphenyl-linker conjugate in the trihydroxyphenyl-linker conjugate solution can be any concentration. The concentration of the trihydroxyphenyl-linker conjugate is typically chosen such that the trihydroxyphenyl-linker conjugate is fully soluble in a chosen solvent, without forming a saturated solution. Exemplary trihydroxyphenyl-linker conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml or about 3 mg/ml.

The primed substrate can be contacted with and/or immersed in the solution of the trihydroxyphenyl-linker conjugate for any duration suitable to couple the trihydroxyphenyl-linker conjugate to the primed substrate. It is believed that the trihydroxyphenyl-linker conjugate can couple to the primed substrate through either one or both of the end group of the linker compound distal from the trihydroxyphenyl group and any residual reactive groups on the trihydroxyphenyl group. In embodiments of the invention the duration of contact can be any duration of time suitable for forming a covalent bond between one or more of the linker or trihydroxyphenyl group with a reactive moiety (when present) on the primed substrate surface. The rate of the coupling of the trihydroxyphenyl-linker conjugate and the primed substrate can depend, in part, on the concentration of the trihydroxyphenyl-linker conjugate solution thereof, the substrate surface to solution volume ratio, the ionic strength of the solution, the pH of the solution, and the temperature. The duration of contact of the primed substrate with the solution of trihydroxyphenyl-linker conjugate can be varied for any suitable time period for coupling the trihydroxyphenyl-linker conjugate to the primed substrate, for example, when using dip coating, from about 10 seconds to about 24 hours. When the duration of contact of the primed substrate with the solution of trihydroxyphenyl-linker conjugate increases above 24 hours (and one of the foregoing exemplary concentrations of trihydroxyphenyl-linker conjugate is used), little difference in the amount of trihydroxyphenyl-linker conjugate coupled to the primed substrate surface is expected (relative to a 24 hour exposure time). Without intending to be bound by theory while, it is believed that the trihydroxyphenyl-linker conjugate may continue to be coupled to the primed substrate, it is expected that the amount of the trihydroxyphenyl-linker conjugate provided after 24 hours will have little effect on the amount of active agent that is ultimately immobilized on the substrate surface, and further, it is believed that the likelihood of the trihydroxyphenyl group self-polymerizing or cross-linking, and therefore gelling of the solution, even at low concentrations, increases with time.

Active Agents

The active agent can include, but is not limited to antimicrobial agents, such as antibacterial agents, antifouling agents, anti-inflammatory agents, such as complement inhibitors, including but not limited to C1 inhibitors, e.g., eculizumab, and C5 inhibitors, anti-thrombogenic agents, such as anti-coagulating agents, and combinations thereof. For example, the active agent can include, but is not limited to, chitosan, dextran, linear polyethylene glycol (PEG), looped polyethylene glycol (PEG), polyethylene glycol derivatives including, but not limited to thiol-terminated PEG, N-hydroxysuccinimide(NHS)-terminated PEG and amine-terminated PEG, poly(N-vinylpyrrolidone) (PVP) and PVP derivatives including, but not limited to, thiol-terminated PVP, amine-terminated PVP, and carboxyl-terminated PVP, heparin, fractionated heparin, and unfractionated heparin, and heparin derivatives, said heparin derivatives including but not limited to, enoxaparin, dalteparin, and tinzaparin, quaternary ammonium polymers, albumin, polyethylenimine, 4-hydroxycoumarin derivatives such as warfarin, coumatetralyl, phenprocoumon, acenocoumarol, dicoumarol, tioclomarol, and brodifacoum, and combinations of the foregoing. In embodiments comprising polyethylene glycol, chitosan, or heparin, the molecular weight can be in a range of about 500 Da to about 1,000,000 Da, or about 1000 Da to about 500,000 Da, about 2000 Da to about 500,000 Da, about 2000 Da to about 250,000 Da, and/or about 2000 Da to about 100,000 Da. In general, the active agent includes a functional group. Suitable functional groups include, but are not limited to, nucleophilic groups. Nucleophilic groups are well known in the art and can include, but are not limited to, hydroxyl, alkoxide, amine, nitrite, thiol, thiolate, imidazole, and combinations thereof. Nucleophilic groups on chitosan include amine and hydroxyl groups; nucleophilic groups on PEG and/or PEG derivatives include hydroxyl groups, thiol groups, amine groups; reactive groups on PVP derivatives include carboxyl groups, thiol groups, amine groups; nucleophilic groups on heparin and heparin derivatives include hydroxyl, carboxylate, and sulfate. The thiol, amine, and carboxyl-terminated PVP derivatives can be prepared by terminating PVP polymerization with an appropriate chain transfer agent such as, for example, mercaptoacetic acid or mercaptoethylamine, or by further derivatizing a carboxyl-terminated PVP such as, for example, by reacting the carboxyl-terminated PVP with cysteamine followed by a reducing agent such as tris(2-carboxyethyl)phosphine (TCEP) or dithiothreitol (DTT).

It is believed that, upon exposure of the trihydroxyphenyl-treated substrate to an active agent, any sites of reactivity available on the trihydroxyphenyl group (i.e., reactive groups and/or unsubstituted carbons on the phenyl ring), or linker compound thereon, can couple to the active agent, thereby immobilizing the active agent on the substrate surface. The active agent adsorbs to/adheres to/couples to/associates with the trihydroxyphenyl group through covalent bond formation, hydrogen bond formation, ionic bond formation, van der Waals interactions, or combinations of the foregoing. Typically, the active agent is coupled to the compound including a trihydroxyphenyl group by forming one or more covalent bonds with an unsubstituted carbon on the trihydroxyphenyl group or through a reactive group on the trihydroxyphenyl group. The reactive group on the trihydroxyphenyl group can be any reactive group that can react with a nucleophile on an active agent. Suitable reactive groups on the trihydroxyphenyl group include, but are not limited to, carboxyls, carboxylates, amides, acyl halides, aldehydes, and esters. The reactive group on the trihydroxyphenyl group can couple to the linker compound, for example, by transesterification or transamidification. The transesterification or transamidification can optionally be promoted by an activator compound such as N,N'-dicyclohexylcarbodiimide (DCC), N,N'-diisopropylcarbodiimide (DIC), hydroxybenzotriazole (HOBt), or 1-hydroxy-7-azabenzotriazole (HOAt). In embodiments wherein a covalent bond forms between the active agent and an unsubstituted carbon of the phenyl ring of the trihydroxyphenyl group, it is believed the covalent bond may be formed by Michael addition. For example, the active agent chitosan can couple to a trihydroxyphenyl group through a hydroxyl or amine group on the active agent that covalently binds with an unsubstituted carbon on the phenyl ring of the trihydroxyphenyl group. Other suitable active agents necessarily include a similar nucleophilic group and therefore can also couple to the compound including a trihydroxyphenyl group in a similar fashion as chitosan.

In one embodiment of the invention, the active agent is coupled to the trihydroxyphenyl-treated primed substrate surface by contacting the trihydroxyphenyl-treated primed substrate surface with the active agent. The active agent can be provided in solution or, if the active agent is a liquid, the active agent can be provided neat. The trihydroxyphenyl-treated primed substrate can be completely immersed in the solution of the active agent, for example, by dip coating. Alternatively, a solution of primer compound can be sprayed or cast onto the trihydroxyphenyl-treated primed substrate, for example, by spin casting or spraying a solution such as an aerosolized solution. For substrates having an interior lumen, such as tubing, the solution can be flowed into the lumen to coat the interior thereof.

The active agent solution solvent can be any solvent that is capable of serving as a carrier for the active agent. For example, most frequently water is used, but other solvents including but not limited to, alcohols, diols, organosulfurs such as sulfolane, ethers, such as diethyl ether and tetrahydrofuran, halocarbons, such as chloroform and dichloromethane, and combinations of the foregoing can also be used. In one embodiment of the methods disclosed herein, the solution of active agent is at a pH in a range of about 5.5 to about 8.5, or about 6 to about 8, or about 7.5, when coupling the active agent to a trihydroxyphenyl group or a linker compound. The solution of the active agent may further include a buffer in order to maintain the pH within the foregoing ranges as is well known in the art. Suitable buffers for maintaining such a pH, include, but are not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), 4-2-hydroxyethyl-1-piperazineethanesulfonic acid (HEPES), and N-tris(hydroxymethyl)methylglycine (Tricine). Of course, one or more of carbonate, phosphate and other known buffer systems for maintaining relatively higher pH values can also be used.

In alternative embodiments, the trihydroxyphenyl-treated primed substrate can be contacted with solutions of active agents having a lower pH. For example, the solution of active agent can be at a pH in a range of about 4 to about 5.5, for example about 4.0, about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5, when coupling the active agent to a trihydroxyphenyl group or a linker compound. Suitable active agents for coupling at lower pH include, but are not limited to, heparin and chitosan. The solution of the active agent may further include a buffer in order to maintain the pH within the foregoing ranges as is well known in the art. Suitable buffers for maintaining such a pH include one or more of acetate, citrate, lactate, phosphate and other known buffer systems can also be used.

The concentration of the active agent in the active agent solution can generally be any concentration. The concentration of the active agent is typically chosen such that the active agent is fully soluble in a chosen solvent, without forming a saturated active agent solution. Higher concentrations are generally preferred to reduce the time needed to couple the active agent to the trihydroxyphenyl group. Exemplary active agent concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml.

The trihydroxyphenyl-treated primed substrate can be contacted with and/or immersed in the active agent or solution of active agent for any duration of time suitable to couple the active agent and the trihydroxyphenyl group of the trihydroxyphenyl-treated substrate. The rate of the coupling of the active agent to the trihydroxyphenyl-treated primed substrate can depend, in part, on the concentration of the active agent in the active agent solution, the substrate surface to solution volume ratio, the ionic strength of the solution, and the temperature. The duration of contact of the trihydroxyphenyl-treated substrate with the active agent or solution of active agent can be varied for any suitable time period for providing a layer on a substrate, for example when using dip coating, from about 10 seconds to about 24 hours. When the duration of contact of the trihydroxyphenyl-treated primed substrate with the solution of active agent increases above 24 hours (and one of the foregoing exemplary concentrations of active agent is used), little difference in the amount of active agent immobilized to the substrate surface is expected (relative to a 24 hour exposure time). Without intending to be bound by theory, while it is believed that while the active agent may continue to be immobilized on the trihydroxyphenyl-treated primed substrate, it is expected that the amount of the active agent immobilized after 24 hours will have little effect on the activity (antibacterial, antimicrobial, etc.) of the resulting substrate having an active agent immobilized thereto.

In embodiments of the invention where the compound including a trihydroxyphenyl group comprises a trihydroxyphenyl-linker conjugate, the active agent can adsorb to/adhere to/couple to/associate with a linker coupled to the trihydroxyphenyl group through covalent bond formation, hydrogen bond formation, ionic bond formation, van der Waals interactions, or combinations of the foregoing. Typically, the active agent is coupled to the linker that is coupled to a trihydroxyphenyl group by forming one or more covalent bonds with the end group of the linker compound distal from the trihydroxyphenyl group. When the group of the linker compound that will couple to the active agent is a reactive group including, but not limited to, carboxyls, carboxylates, amides, acyl halides, aldehydes, and esters, it is believed that the linker is coupled to the active agent through the reactive group on the linker and a nucleophilic group on the active agent. It is further believed that when the end group of the linker that will couple to the active agent is a nucleophile such as hydroxyl, alkoxide, amine, nitrite, thiol, and thiolate, the linker can couple to an active agent, including but not limited to heparin, chitosan, quaternary chitosan, etc.

As described above, "active agent" encompasses active agent-linker conjugates. In embodiments of the invention where the active agent comprises an active agent-linker conjugate, an active agent-linker conjugate is initially formed by coupling a nucleophile on the linker compound with a reactive group of an active agent or by coupling a nucleophile on an active agent with a reactive group on a linker compound, followed by contacting the trihydroxyphenyl-treated substrate with a solution of the active agent-linker conjugate. The active agent adsorbs to/adheres/couples to/associates with a linker compound through covalent bond formation, hydrogen bond formation, ionic bond formation, van der Waals interactions, or combinations of the foregoing. The linker compound can be any linker compound as previously described herein. Typically, the active agent is coupled to a linker compound by forming one or more covalent bonds with an end group of the linker compound. It is believed that when the linker couples to the active agent through a reactive group including, but not limited to, carboxyls, carboxylates, amides, acyl halides, aldehydes, and esters, the linker is coupled to the active agent through the reactive group on the linker and a nucleophilic group on the active agent. It is further believed that when the reactive group of the linker is a nucleophile such as hydroxyl, alkoxide, amine, nitrite, thiol, and thiolate, the linker can couple to a reactive group of an active agent, including but not limited to heparin, chitosan, quaternary chitosan, etc., through the nucleophilic group on the linker compound.

The active agent-linker conjugate can be formed by combining in solution a linker compound and an active agent. The solution of the active agent and/or the linker compound can be prepared in any solvent capable of acting as a carrier for the active agent and/or the linker compound. For example, most frequently water is used, but other solvents including but not limited to, alcohols, diols, ethers, such as diethyl ether and tetrahydrofuran, halocarbons, such as chloroform and dichloromethane, and combinations of the foregoing can also be used.

In refinements of the aforementioned embodiment, the solution of active agent and/or linker compound is at a pH in a range of about 5.5 to about 9.5, or about 8 to about 9, or about 8.5 or about 6 to about 8, or about 7.5. The solution of active agent and/or solution of linker compound may further include a buffer in order to maintain the pH within the foregoing ranges, including, but not limited to, N,N-bis (2-hydroxyethyl)glycine (Bicine), 3-{[tris(hydroxymethyl) methyl]amino}propanesulfonic acid (TAPS), tris(hydroxymethyl)methylamine (Tris), and N-tris (hydroxymethyl)methylglycine (Tricine). Of course, one or more of citrate, carbonate, lactate, phosphate and other known buffer systems can also be used.

In alternative embodiments, the solutions of active agent and/or linker compound can be maintained at a lower pH. For example, acetate buffered solutions can be used, having a pH in a range of about 4 to about 5.5, about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5, when coupling the active agent to the linker compound to form the active agent-linker conjugate. Suitable active agents for coupling to linker compounds at lower pH include, but are not limited to, heparin and chitosan. The solutions of active agent and/or linker compound may further include a buffer in order to maintain the pH within the foregoing ranges as is well known in the art. Suitable buffers for maintaining such a pH include one or more of acetate, citrate, lactate, and other known buffer systems can also be used.

The concentrations of the active agent and linker compound in solution can be any concentration. In some embodiments, the active agent can be directly added to a solution of the linker compound, without first forming an active agent solution. In alternative embodiments, the active agent can be provided to a solution of the linker compound in an active agent solution. The concentrations are typically chosen such that the active agent and/or linker compound are fully soluble in a chosen solvent, without forming saturated solutions. Exemplary active agent and/or linker compound concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of active agent to linker compound can be in a range of about 8:1 to about 8:1, about 1:7 to about 7:1, about 1:6 to about 6:1, about 1:5 to about 5:1, about 1:4 to about 4:1, about 1:3 to about 3:1, and/or about 1:2 to about 2:1, for example about 1:1.

The active agent-linker conjugate can be coupled to the trihydroxyphenyl-treated primed substrate by contacting the trihydroxyphenyl-treated primed substrate with a solution of active agent-linker conjugate. The trihydroxyphenyl-treated primed substrate can be completely immersed in the solution of the active agent-linker conjugate, for example, by dip coating. Alternatively, a solution of the active agent-linker conjugate can be sprayed or cast onto the primed substrate, for example, by spin casting or spraying a solution such as an aerosolized solution. For substrates having an interior lumen, such as tubing, the solution can be flowed into the lumen to coat the interior thereof.

The concentration of the active agent-linker conjugate in the active agent-linker conjugate solution can be any concentration. The concentration of the active agent-linker conjugate is typically chosen such that the active agent-linker conjugate is fully soluble in a chosen solvent, without forming a saturated solution. Exemplary active agent-linker conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml.

The trihydroxyphenyl-treated primed substrate can be contacted with and/or immersed in the solution of the active agent-linker conjugate for any duration suitable to couple the active agent-linker conjugate to the trihydroxyphenyl treated primed substrate. It is believed that the active agent-linker conjugate can couple to the trihydroxyphenyl-treated primed substrate through either or both of the end group of the linker compound distal from the active agent and residual nucleophilic groups on the active agent. It is further believed that the active agent-trihydroxyphenyl conjugate can couple to either or both of the trihydroxyphenyl group and the primer compound of the trihydroxyphenyl-treated primed substrate. In embodiments of the invention the duration of contact can be any duration of time suitable for forming a covalent bond between one or more of the linker or active agent with one or more of the primer compound and/or the trihydroxyphenyl group of the trihydroxyphenyl-treated primed substrate. The rate of the coupling of the active agent-linker conjugate to the trihydroxyphenyl-treated primed substrate can depend, in part, on the concentration of the active agent-linker conjugate solution thereof, the substrate surface to solution volume ratio, the ionic strength of the solution, the pH of the solution, and the temperature. The duration of contact of the trihydroxyphenyl-treated primed substrate with the solution of active agent-linker conjugate can be varied for any suitable time period for coupling the active agent-linker conjugate to the trihydroxyphenyl-treated primed substrate, for example, when using dip coating, from about, about 10 seconds to about 24 hours. When the duration of contact of the substrate with the solution of active agent-linker conjugate increases above 24 hours (and one of the foregoing exemplary concentrations of active agent-linker conjugate is used), little difference in the amount of active agent immobilized to the substrate surface is expected (relative to a 24 hour exposure time). Without intending to be bound by theory, while it is believed that while the active agent-linker conjugate may continue to be immobilized on the substrate, it is expected that the amount of the active agent immobilized after 24 hours will have little effect on the activity (antibacterial, antimicrobial, etc.) of the resulting substrate having an active agent immobilized thereto.

Active Agent—Trihydroxyphenyl Conjugates with Optional Linker

In embodiments of the invention, an active agent-trihydroxyphenyl conjugate is initially formed by coupling a nucleophile of the active agent with a reactive group on the trihydroxyphenyl group or by coupling a nucleophile of the trihydroxyphenyl group with a reactive group of the active agent, followed by contacting the primed substrate with a solution of the active agent-trihydroxyphenyl conjugate. The active agent-trihydroxyphenyl conjugate can be formed by combining in solution a compound including a trihydroxyphenyl group and an active agent. As described previously, the compound including a trihydroxyphenyl group includes trihydroxyphenyl-linker conjugates. Therefore, the active agent-trihydroxyphenyl conjugate encompasses active agents coupled to linker compounds that are further coupled to trihydroxyphenyl groups. Active agents coupled to linker compounds can be formed as described above for active agent-linker conjugates and compounds including trihydroxyphenyl groups coupled to linker compounds can be formed as described above for trihydroxyphenyl-linker conjugates. These can then be further reacted with a compound including trihydroxyphenyl group or active agent, respectively, to form active agent-trihydroxyphenyl conjugates. Generic active agent-trihydroxyphenyl conjugates can be represented by formulae (Va-c) and (VIa-c):

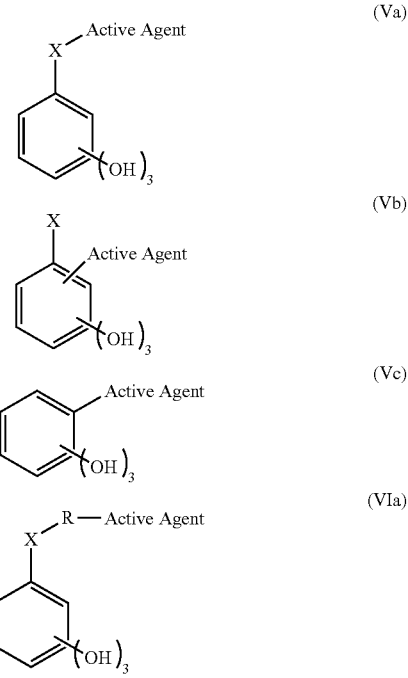

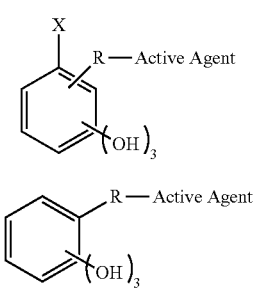

wherein X can be halogen, amine, thiol, aldehyde, carboxylic acid, carboxylate, acyl halide, ester, acrylate, vinyl, C1 to C10 branched or linear alkyl amine, C1 to C10 branched or linear alkyl thiol, C1 to C10 branched or linear alkyl aldehyde, C1 to C10 branched or linear alkyl carboxylic acid, C1 to C10 branched or linear alkyl carboxylate, C1 to C10 branched or linear alkyl acyl halide, C1 to C10 branched or linear alkyl ester, or C1 to C10 branched or linear alkyl acrylate, and R is a linker compound. With respect to the length of the carbon chains of the listed substituents, the chain length is typically C1 to C5 when aqueous solutions are used (as long as solubility is achieved in the selected aqueous system); when organic solvents are used, the chain length can be C1 to C10. In accordance with compounds (Va-c) and (VIa-c), the three hydroxyl groups can be provided on any three of $C_2$, $C_3$, $C_4$, $C_5$, and $C_6$. For example, when the compound including a trihydroxyphenyl group is a carboxylic acid such as gallic acid (and thus X is carboxyl), the active agent-trihydroxyphenyl conjugate can be of formula (Va), (Vb), (VIa), or (VIb):

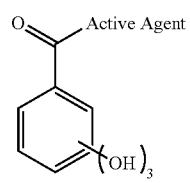

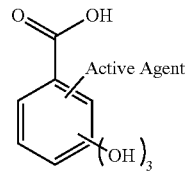

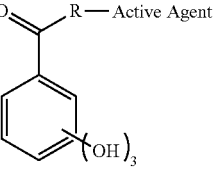

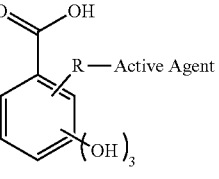

wherein R is the linker compound and Active Agent denotes an active agent. Further, when the compound including a trihydroxyphenyl group is gallic acid, consistent with the active agent-trihydroxyphenyl conjugates according to (Va), (Vb), (VIa), and (VIb), the three hydroxyl groups are provided on $C_3$, $C_4$, and $C_5$, and the linker is provided on the carboxyl group (IVa) or one of $C_2$ or $C_6$ (IVb). When the compound including a trihydroxyphenyl group is pyrogallol, the active agent-trihydroxyphenyl conjugate can be of formula (Vc) or (VIc):

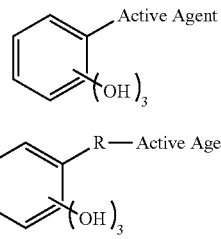

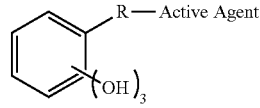

wherein R is the linker compound and the three hydroxyl groups can be provided on any consecutive three of $C_2$, $C_3$, $C_4$, $C_5$, and $C_6$.

In embodiments of the invention wherein the active agent is provided as a neat liquid, the active agent can be the solvent in which the active agent-trihydroxyphenyl conjugate is formed. In embodiments of the invention wherein a solution of an active agent is combined with a solution of a compound including a trihydroxyphenyl group, the solution of the active agent and/or the compound including a trihydroxyphenyl group can be prepared in any solvent capable of acting as a carrier for the active agent and/or the compound including a trihydroxyphenyl group. For example, most frequently water is used, but organic solvents including but not limited to, alcohols, diols, organosulfurs such as sulfolane, ethers, such as diethyl ether and tetrahydrofuran, alkanes, aromatics halocarbons, such as chloroform and dichloromethane, and combinations of the foregoing can also be used.

In refinements of the aforementioned embodiment, the solution of active agent and/or solution of compound including a trihydroxyphenyl group is at a pH in a range of about 7.5 to about 9.5, or about 8 to about 9, or about 8.5. The solution of active agent and/or solution of compound including a trihydroxyphenyl group may further include a buffer in order to maintain the pH within the foregoing ranges, including, but not limited to, N,N-bis(2-hydroxyethyl)glycine (Bicine), 3-{[tris(hydroxymethyl)methyl]amino}propanesulfonic acid (TAPS), tris(hydroxymethyl)methylamine (Tris), and N-tris(hydroxymethyl)methylglycine (Tricine). Of course, one or more of citrate, carbonate, lactate, phosphate and other known buffer systems can also be used. In alternative embodiments, solution of active agent and/or solution of compound including a trihydroxyphenyl group can have a lower pH. For example, acetate buffered solutions can be used for deposition of active agents at a pH in a range of about 4 to about 5.5, about 4.1, about 4.2, about 4.3, about 4.4, about 4.5, about 4.6, about 4.7, about 4.8, about 4.9, about 5, about 5.1, about 5.2, about 5.3, about 5.4, and/or about 5.5. Suitable active agents for coupling to a compound including a trihydroxyphenyl group in solution at lower pH include, but are not limited to, heparin.

The concentrations of the active agent and compound including a trihydroxyphenyl group in solution can generally be any concentration. In some embodiments, the active agent can be directly added to a solution of the compound including a trihydroxyphenyl group, without first forming an active agent solution. In alternative embodiments, the active agent can be provided to a solution of the compound including a trihydroxyphenyl group in an active agent solution. The concentrations are typically chosen such that the active agent and/or compound including a trihydroxyphenyl group are fully soluble in a chosen solvent, without forming saturated solutions. Exemplary active agent and/or compound including a trihydroxyphenyl group concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml. The ratio of active agent to compound including a trihydroxyphenyl group can vary depending on if the active agent is a small molecule or a polymer, as well as if the compound including a trihydroxyphenyl group is a small molecule or a polymer. For example, when the active agent is a polymer and the compound including a trihydroxyphenyl group is a small molecule, one active agent could couple thousands of compounds including a trihydroxyphenyl group. Alternatively, when the active agent is a small molecule and the compound including a trihydroxyphenyl group is a polymer, one compound including a trihydroxyphenyl group could couple to thousands of active agents. Suitable ratios of active agents to compounds including a trihydroxyphenyl can, therefore, be in a range of about 1:5,000 to about 5,000:1, including all intermediate ranges, such as about 1:5 to about 5:1, about 1:4 to about 4:1, about 1:3 to about 3:1, and/or about 1:2 to about 2:1, for example about 1:1.

The active agent-trihydroxyphenyl conjugate can be coupled to the primed substrate by contacting the primed substrate with a solution of active agent-trihydroxyphenyl conjugate. The primed substrate can be completely immersed in the solution of the active agent-trihydroxyphenyl conjugate, for example, by dip coating. Alternatively, a solution of the active agent-trihydroxyphenyl conjugate can be sprayed or cast onto the primed substrate, for example, by spin casting or spraying, using a solution such as an aerosolized solution. For substrates having an interior lumen, such as tubing, the solution can be flowed into the lumen to coat the interior thereof.

The concentration of the active agent-trihydroxyphenyl conjugate in the active agent-trihydroxyphenyl conjugate solution can be any concentration. The concentration of the active agent-trihydroxyphenyl conjugate is typically chosen such that the active agent-trihydroxyphenyl conjugate is fully soluble in a chosen solvent, without forming a saturated solution. Exemplary active agent-trihydroxyphenyl conjugate concentrations can be in a range of about 0.0001 to about 100 mg/ml, about 0.001 to about 100 mg/ml, about 0.01 to about 100 mg/ml, about 0.05 to about 100 mg/ml, 0.0001 to about 90 mg/ml, about 0.0001 to about 80 mg/ml, about 0.0001 to about 70 mg/ml, about 0.0001 to about 60 mg/ml, about 0.0001 to about 50 mg/ml, about 0.001 to about 50 mg/ml, about 0.001 to about 40 mg/ml, about 0.001 to about 30 mg/ml, about 0.01 to about 30 mg/ml, about 0.01 to about 20 mg/ml, about 0.01 to about 15 mg/ml, about 0.01 to about 10 mg/ml, about 0.01 to about 5 mg/ml, about 0.05 to about 5 mg/ml, and/or about 0.05 to about 3 mg/ml, for example, about 1 mg/ml, about 1.5 mg/ml and/or about 3 mg/ml.

The primed substrate can be contacted with and/or immersed in the solution of the active agent-trihydroxyphenyl conjugate for any duration of time suitable to couple the trihydroxyphenyl group of the active agent-trihydroxyphenyl conjugate to the primed substrate. In embodiments of the invention the duration can be any duration of time suitable for forming a network of the primer compound and the trihydroxyphenyl of the active agent-trihydroxyphenyl conjugate. The rate of the coupling of the active agent-trihydroxyphenyl conjugate and the primed substrate can depend, in part, on the concentration of the active agent-trihydroxyphenyl conjugate in the active agent-trihydroxyphenyl conjugate solution, the substrate surface to solution volume ratio, the ionic strength of the solution, the pH of the solution, and the temperature. The duration of contact of the primed substrate with the solution of active agent-trihydroxyphenyl conjugate can be varied for any suitable time period for coupling the trihydroxyphenyl group with the primed substrate, for example, when using dip coating, from about 10 seconds to about 24 hours. When the duration of contact of the substrate with the solution of active agent-trihydroxyphenyl conjugate increases above 24 hours (and one of the foregoing exemplary concentrations of active agent-trihydroxyphenyl conjugate is used), little difference in the amount of active agent immobilized to the substrate surface is expected (relative to a 24 hour exposure time). Without intending to be bound by theory, while it is believed that while the active agent-trihydroxyphenyl conjugate may continue to be immobilized on the substrate, it is expected that the amount of the active agent immobilized after 24 hours will have little effect on the activity (antibacterial, antimicrobial) of the resulting substrate having an active agent immobilized thereto.

The methods, substrates, and medical devices in accordance with the invention can be better understood in light of the following examples, which are merely intended to illustrate the methods, substrates, and medical devices and are not meant to limit the scope thereof in any way.

EXAMPLES

Example 1

Effect of Heparin Concentration on the Immobilization of Heparin onto Polysulfone Substrates An anti-thrombogenic agent, heparin, was immobilized onto polysulfone substrates. The effect of heparin concentration on the immobilization of heparin on a polysulfone substrate was analyzed by varying the concentration of heparin in the heparin solution. The concentration of heparin in the heparin solution was either 0.1 mg/mL, 1.0 mg/mL, or 5.0 mg/mL. The substrates were prepared as followed.

A polysulfone substrate was immersed in a solution of chitooligosaccharide primer compound (1 mg/mL, 10,000 Mw) dissolved in 10 mM Bicine (pH 8.5). The solution with the polysulfone substrate immersed therein was mildly agitated at room temperature for 24 hours. The substrate was removed from the solution and rinsed with filtered, distilled water. The resulting primed substrate was immersed in a solution of gallic acid (1 mg/mL), dissolved in 10 mM Bicine (pH 8.5). The gallic acid solution with the primed-substrate immersed therein was mildly agitated at room temperature for 24 hours. The substrate was removed from the gallic acid solution and rinsed with filtered, distilled water. The resulting gallic acid treated primed substrate was immersed in a solution of heparin (0.1 mg/mL, 1.0 mg/mL, or 5.0 mg/mL heparin) dissolved in 10 mM to 300 mM acetate (pH 4.5), supplemented with 600 mM NaCl. The solution of heparin with the gallic acid treated primed substrate immersed therein was mildly agitated for 24 hours. The substrate was removed from the solution of heparin and rinsed with filtered, distilled water, resulting in a polysulfone substrate with heparin immobilized on the surface thereof.

Thus, Example 1 illustrates the immobilization of heparin onto a polysulfone substrate according to the invention. Immobilization of heparin was confirmed using XPS and through Alcian blue staining of the anionic heparin immobilized on the substrate surface.

FIG. 1 shows the x-ray photoelectron spectroscopy survey spectra of polysulfone surfaces modified with chitooligosaccharide, gallic acid and different levels of heparin. "PS" is an untreated polysulfone surface, "GA" is a polysulfone substrate with chitooligosaccharide and gallic acid, prepared according to Example 1. "0.1" is a polysulfone substrate modified with chitooligosaccharide, gallic acid and a 0.1 mg/mL heparin solution, prepared according to Example 1. "1.0" is a polysulfone substrate modified with chitooligosaccharide, gallic acid and a 1.0 mg/mL heparin solution, prepared according to Example 1. "5.0" is a polysulfone substrate modified with chitooligosaccharide, gallic acid and a 5.0 mg/mL heparin solution, prepared according to Example 1. O1s designates oxygen signals, N1s designates nitrogen signals, C1s designates carbon signals, and S2s and S2p designate sulfur signals. The N1s signals are observed on all surfaces including a chitooligosaccharide-gallic acid layer. The S1s and S2p peaks are not present in the "GA" trace, indicating a layer of chitooligosaccharide and gallic acid has been deposited on the substrate surface. The S1s and S2p peaks present in the "0.1", "1.0", and "5.0" traces confirms that heparin has been immobilized on the substrate.

The elemental composition can be obtained from the XPS analysis and the compositional data is provided in the following table.

| Group | C (%) | O (%) | N (%) | S (%) |
|-------|-------|-------|-------|-------|
| PS    | 83.6  | 12.8  | 0.0   | 3.6   |
| GA    | 62.4  | 32.2  | 4.9   | 0.6   |
| 0.1   | 63.1  | 30.2  | 3.6   | 3.1   |
| 1.0   | 53.0  | 38.2  | 5.1   | 3.7   |
| 5.0   | 62.4  | 30.7  | 3.8   | 3.2   |

The elemental data further suggests that the amount of heparin immobilized on a substrate submerged in a heparin solution for 24 hours, as determined by the percentage of sulfur detected, is not strongly dependent on the concentration, in the range tested, of heparin in the heparin solution.

Example 2

Immobilization of Heparin onto Polysulfone Substrate

An anti-thrombogenic agent, heparin, was immobilized onto a polysulfone substrate. A polysulfone substrate was immersed in a solution of chitooligosaccharide primer compound (1 mg/mL, 10,000 Mw) dissolved in 10 mM Bicine buffer (pH of 8.4). The solution with the polysulfone substrate immersed therein was mildly agitated at room temperature for 90 minutes. The substrate was removed from the solution and rinsed with filtered, distilled water. The resulting primed substrate was immersed in a solution of gallic acid (1.5 mg/mL) in 100 mM Bicine buffer (pH 7.6). The gallic acid solution with the primed-substrate immersed therein was mildly agitated at room temperature for 90 minutes. The substrate was removed from the gallic acid solution and rinsed with filtered, distilled water. The resulting gallic acid treated primed substrate was immersed in a solution of heparin (1 mg/mL) in 0.3 M sodium acetate and 0.6 M sodium chloride solution. The solution of heparin with the gallic acid treated primed substrate immersed therein was mildly agitated for about 12 hours. The substrate was removed from the solution of heparin and rinsed with filtered, distilled water resulting in a polysulfone substrate with heparin immobilized on the surface thereof. Immobilization of heparin was confirmed using Alcian blue staining of the anionic heparin immobilized on the substrate, as described in Example 10.

Thus, Example 2 illustrates the immobilization of heparin onto a polysulfone substrate according to the invention.

Example 3

Antithrombotic Activity of a Polysulfone Substrate with Heparin Immobilized Thereto An antithrombogenic agent, heparin, was immobilized onto a polysulfone substrate. A polysulfone substrate was immersed in a solution of chitooligosaccharide primer compound (1.3 mg/mL, 10,000 Mw) dissolved in 10 mM Bicine buffer (pH of 8.4). The solution with the polysulfone substrate immersed therein was mildly agitated at room temperature for 15 minutes. The substrate was removed from the solution and rinsed with filtered, distilled water. The resulting primed substrate was immersed in a solution of gallic acid (3.5 mg/mL) dissolved in 100 mM Bicine buffer (pH of 7.7). The gallic acid solution with the primed-substrate immersed therein was mildly agitated at room temperature for 30 minutes. The substrate was removed from the gallic acid solution and rinsed with filtered, distilled water. The resulting gallic acid treated primed substrate was immersed in a solution of heparin (1.1 mg/mL) in 0.3 M sodium acetate and 0.6 M sodium chloride solution. The solution of heparin with the gallic acid treated primed substrate immersed therein was mildly agitated for 30 minutes. The substrate was removed from the solution of heparin and allowed to dry, resulting in a polysulfone substrate with heparin immobilized on the surface thereof.

Figure 2:
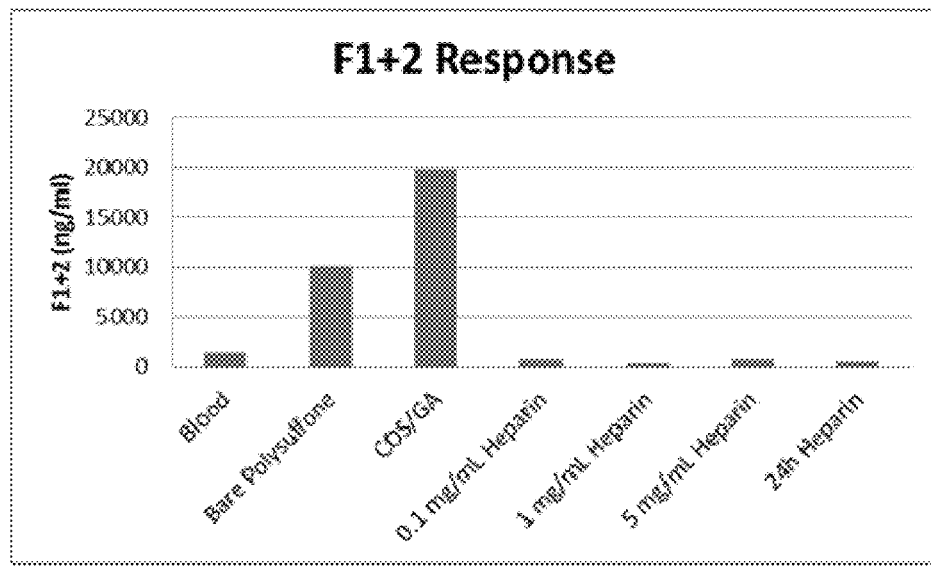
FIG. 2 shows a plot of thrombin conversion (ng/ml) vs. time (minutes) for different substrates relative to a control.

The antithrombogenic activity of a polysulfone substrate with heparin immobilized thereto was evaluated by determining the conversion of prothrombin to thrombin in a blood sample. The conversion of prothrombin to thrombin in a blood sample containing an uncoated polysulfone substrate (designated PS), a gallic acid treated primed control substrate (prepared according to the procedure for forming the gallic acid treated primed substrate in Example 5, designated COS/GA), and a sample containing a polysulfone substrate with the active agent heparin immobilized thereto according to the invention (designated 1 mg/mL Heparin) were determined and compared to the thrombin conversion in a control blood sample (designated Blood). As shown in FIG. 2, when polysulfone substrates are incubated in blood, the blood sample comprising the uncoated polysulfone substrate does not demonstrate reduced thrombin conversion relative to the control blood sample. In contrast, the blood sample comprising the polysulfone substrate with heparin immobilized thereto (1 mg/mL Heparin) shows improved antithrombogenic activity relative to both the sample comprising the untreated polysulfone substrate and the control blood sample.

F 1+2 was measured using the Siemens Enzygnost® F1+2 (monoclonal) assay kit. The F1+2 fragment is formed during the conversion of prothrombin into active thrombin, during the coagulation cascade. Measurement of the F1+2 fragment allows for quantification of thrombin formed. The F1+2 levels were determined by incubating the polysulfone substrates in 2 mL of human blood containing 0.4 U/mL of heparin with slight agitation for 2 hours. Aliquots of the blood samples were taken over the 2 hours to determine the conversion of thrombin over time. The blood samples were then run according to the Siemens Enzygnost® F1+2 (monoclonal) assay kit package insert for determination of F1+2.

Thus, Example 3 demonstrates the immobilization of heparin onto a polysulfone substrate and the retained activity of the heparin after its immobilization. While a polysulfone substrate without heparin, PS, was fouled by thrombin and a gallic acid treated primed control substrate, COS/GA, was fouled by thrombin, the polysulfone substrate treated with heparin, 1 mg/mL Heparin, advantageously demonstrates reduced thrombin conversion relative to PS, thereby confirming the immobilization of heparin, an antithrombogenic agent, on the substrate surface and the retention of its activity after immobilization on that surface.

Example 4

Antithrombotic Activity of a Polysulfone Substrate with Heparin Immobilized Thereto An antithrombogenic agent, heparin, was immobilized onto a polysulfone substrate. A polysulfone substrate was immersed in a solution of chitooligosaccharide primer compound (0.1 mg/mL, 10,000 Mw) dissolved in 10 mM Bicine buffer (pH of 8.4). The solution with the polysulfone substrate immersed therein was mildly agitated at room temperature for 10 minutes. The substrate was removed from the solution. The resulting primed substrate was immersed in a solution of gallic acid (1 mg/mL) dissolved in 100 mM Bicine buffer (pH of 7.7). The gallic acid solution with the primed-substrate immersed therein was mildly agitated at room temperature for 30 minutes. The substrate was removed from the gallic acid solution and rinsed with filtered, distilled water. The resulting gallic acid treated primed substrate was immersed in a solution of heparin (5 mg/mL) in 0.3 M sodium acetate and 0.6 M sodium chloride solution. The solution of heparin with the gallic acid treated primed substrate immersed therein was mildly agitated for 30 minutes. The substrate was removed from the solution of heparin and rinsed with filtered, distilled water, resulting in a polysulfone substrate with heparin immobilized on the surface thereof.

The antithrombogenic activity of a polysulfone substrate heparin immobilized on was evaluated by determining the conversion of prothrombin to thrombin in a blood sample. The conversion of prothrombin to thrombin in a blood sample containing an uncoated polysulfone substrate (designated PS), a gallic acid treated primed control substrate (prepared according to the procedure for forming the gallic acid treated primed substrate in Example 5, designated COS/GA), and a sample containing a polysulfone substrate with the active agent heparin immobilized thereto according to the invention (designated 5 mg/mL Heparin) were determined and compared to the thrombin conversion in a control blood sample (designated Blood). As shown in FIG. 2, when polysulfone substrates are incubated in blood, the blood sample containing the uncoated polysulfone substrate does not demonstrate reduced thrombin conversion. In contrast, the blood sample containing the polysulfone substrate with heparin immobilized thereon shows improved antithrombogenic activity relative to both the sample containing the untreated polysulfone substrate and the control blood sample.

F 1+2 was measured using the Siemens Enzygnost® F1+2 (monoclonal) assay kit, as described in Example 3.

Thus, Example 4 demonstrates the immobilization of heparin onto a polysulfone substrate and the retention of the activity of the heparin after its immobilization. While the polysulfone substrate without heparin, PS, was fouled by thrombin and a gallic acid treated primed control substrate, COS/GA, was fouled by thrombin, the polysulfone substrate treated with heparin, 5 mg/mL Heparin, advantageously demonstrates reduced thrombin conversion relative to PS, thereby confirming the immobilization of heparin, an antithrombogenic agent, on the substrate surface and the retention of its activity after immobilization on that surface.

Example 5

Antithrombotic Activity of a Polysulfone Substrate with Heparin Immobilized Thereto An antithrombogenic agent, heparin, was immobilized onto a polysulfone substrate. A polysulfone substrate was immersed in a solution of chitooligosaccharide primer compound (5 mg/mL, 10,000 MW) dissolved in 10 mM Bicine (pH 8.4). The solution with the polysulfone substrate immersed therein was mildly agitated at room temperature for 24 hours. The substrate was removed from the solution. The resulting primed substrate was immersed in a solution of gallic acid (2.5 mg/mL) dissolved in 100 mM Bicine (pH 7.7). The gallic acid solution with the primed substrate immersed therein was mildly agitated at room temperature for 20 hours. The substrate was removed from the gallic acid solution and rinsed with filtered, distilled water. The resulting gallic acid treated primed substrate was immersed in a solution of heparin (1 mg/mL) in 0.3 M sodium acetate and 0.6 M sodium chloride solution (pH 5.17). The solution of heparin with the gallic acid-treated primed substrate immersed therein was mildly agitated for 24 hours. The substrate was removed from the solution of heparin and rinsed with filtered, distilled water and dried in a laminar flow hood resulting in a polysulfone substrate with heparin immobilized on the surface thereof.

The antithrombogenic activity of a polysulfone substrate with the active agent heparin immobilized thereto according to the invention was evaluated by determining the conversion of prothrombin to thrombin in a blood sample. The conversion of prothrombin to thrombin for a blood sample containing an uncoated polysulfone substrate (designated PS), a gallic acid treated primed control substrate (designated COS/GA), and a sample containing a polysulfone substrate with the active agent heparin immobilized thereto (designated 24 h Heparin) were determined. Each of the foregoing substrates were compared to the thrombin conversion in a control blood sample (designated Blood). The substrates were incubated in blood and the thrombin conversion was determined. As shown in FIG. 2, the untreated polysulfone substrate and the gallic acid treated primed substrate did not demonstrate improved antithrombogenic activity (i.e., reduced thrombin conversion) relative to the control blood sample, however, the polysulfone substrate having heparin immobilized thereto (24 h Heparin) advantageously demonstrated reduced thrombin conversion relative to the untreated polysulfone substrate, thereby confirming the immobilization of heparin, an antithrombogenic agent, on the substrate surface. Further, FIG. 2 shows that a substrate wherein Heparin was immobilized thereto using the same concentration of Heparin but a shorter dip time (1 mg/mL, 30 min, Example 3) had similar antithrombogenic activity compared to a substrate wherein Heparin was immobilized thereto using a 24 hour dip time (24 h Heparin, Example 5).

Thus, Example 5 shows the immobilization of heparin onto a polysulfone substrate and the retention of the activity of the heparin after its immobilization.

Example 6

Stability of Heparin Immobilized on a Polysulfone/Polyisoprene Substrate to Blood and Washing Multi-component polysulfone and polyisoprene flow cells with heparin immobilized thereto according to the invention were prepared as described in Example 5 except a mixture of concentrated HCL: 30% $H_2O_2$.(1:1) was utilized to pretreat the substrate to enhance wettability. The cell was filled with the HCL:peroxide solution and allowed to sit for about 5 min. The cell was then flushed with distilled water. The heparin was then immobilized to the substrate as described in Example 5. The antithrombogenic activity of a polysulfone/polyisoprene substrate with the active agent heparin immobilized thereto according to the invention was evaluated by visual and microscopic investigation. The experiment was set up to compare an unmodified polysulfone/polyisoprene flow cell and a polysulfone/polyisoprene flow cell with heparin immobilized thereto for thrombus formation. Two blood loops were assembled with silicone tubing, a blood reservoir and the polysulfone/polyisoprene flow cell, one loop with the unmodified flow cell and one loop with the heparin modified cell. A roller pump was utilized to provide a flow rate of 50 mL/min in a continuous loop. The loop was filled and primed with about 175 mL of blood, which was recirculated for 2 hours. The same blood source was utilized for both loops to remove variability of donors. After completion of the recirculation the loop was rinsed with saline and then washed with a flow of >400 mL/min water heated to 85° C. for a period of no less than 60 minutes. The two cells were analyzed and then the process repeated out to 3 cycles. After completion of the last cycle, optical analysis showed no visible thrombus on the heparin modified flow cell. In contrast, the unmodified flow cell had large areas of thrombus visible to the naked eye. Analysis using SEM showed a very dense fibrin structure on the unmodified flow cell. In contrast, the heparin modified flow cell contained only a small amount of fibrin structure that was not visible except under high magnification in the SEM.

Thus, Example 6 demonstrates that substrates with the active agent heparin immobilized thereto according to the invention can advantageously be washed and reused.

Example 7

Immobilization of Heparin onto Polycarbonate Substrate Using Chitooligosaccharide as the Primer Compound An antithrombogenic agent, heparin, was immobilized onto a polycarbonate substrate. A polycarbonate substrate was immersed in a solution of chitooligosaccharide primer compound (1 mg/mL, 10,000 Mw) dissolved in 10 mM Bicine buffer (pH of 8.0). The solution with the polycarbonate substrate immersed therein was mildly agitated at room temperature for 24 hours. The substrate was removed from the solution and rinsed with filtered, distilled water. The resulting primed substrate was immersed in a solution of gallic acid (2 mg/mL) in 100 mM Bicine buffer (pH 7.5). The gallic acid solution with the primed-substrate immersed therein was mildly agitated at room temperature for 24 hours. The substrate was removed from the gallic acid solution and rinsed with filtered, distilled water. The resulting gallic acid treated primed substrate was immersed in a solution of heparin (1 mg/mL) in 0.3 M sodium acetate and 0.6 M sodium chloride solution. The solution of heparin with the gallic acid treated primed substrate immersed therein was mildly agitated for about 24 hours. The substrate was removed from the solution of heparin and rinsed with filtered, distilled water resulting in a polycarbonate substrate with heparin immobilized on the surface thereof.

Thus, Example 7 illustrates the immobilization of heparin onto a polycarbonate substrate according to the invention. Immobilization of heparin was confirmed using Alcian blue staining of the anionic heparin immobilized on the substrate, as described in Example 10.

Example 8

Immobilization of Heparin onto Polycarbonate Substrate Using Polyethyleneimine as the Primer Compound An antithrombogenic agent, heparin, was immobilized onto a polycarbonate substrate. A polycarbonate substrate was immersed in a solution of polyethyleneimine (PEI) primer compound (1 mg/mL, 10,000 Mw) dissolved in 10 mM Bicine buffer (pH of 8.0). The solution with the polycarbonate substrate immersed therein was mildly agitated at room temperature for 24 hours. The substrate was removed from the solution and rinsed with filtered, distilled water. The resulting primed substrate was immersed in a solution of gallic acid (2 mg/mL) in 100 mM Bicine buffer (pH 7.5). The gallic acid solution with the primed-substrate immersed therein was mildly agitated at room temperature for 24 hours. The substrate was removed from the gallic acid solution and rinsed with filtered, distilled water. The resulting gallic acid treated primed substrate was immersed in a solution of heparin (1 mg/mL) in 0.3 M sodium acetate and 0.6 M sodium chloride solution. The solution of heparin with the gallic acid treated primed substrate immersed therein was mildly agitated for about 24 hours. The substrate was removed from the solution of heparin and rinsed with filtered, distilled water resulting in a polycarbonate substrate with heparin immobilized on the surface thereof.

Thus, Example 8 illustrates the immobilization of heparin onto a polycarbonate substrate according to the invention.

Immobilization of heparin was confirmed using Alcian blue staining of the anionic heparin immobilized on the substrate, as described in Example 10.

Example 9

Silver Nitrate Test for Confirming the Coupling of the Compound Including a Trihydroxyphenyl Group to the Primer Compound A variety of compounds including a trihydroxyphenyl group (THP) were coupled to a primed polysulfone substrate, and the immobilization of the THP to the substrate was confirmed using a silver nitrate test. A polysulfone substrate was immersed in a solution of chitooligosaccharide primer compound (1 mg/mL, 10,000 Mw) dissolved in 10 mM Bicine buffer (pH of 8.0). The solution with the polysulfone substrate immersed therein was mildly agitated at room temperature for 24 hours. The substrate was removed from the solution and rinsed with filtered, distilled water. The resulting primed substrate was immersed in a solution of one of a compound including a trihydroxyphenyl group (THP), selected from gallic acid (2 mg/mL), pyrogallol (2 mg/mL), or 2,4,6-trihydroxybenzaldehyde (2 mg/mL) dissolved in 100 mM Bicine buffer (pH 7.5). The THP solution with the primed-substrate immersed therein was mildly agitated at room temperature for 24 hours. The substrate was removed from the THP solution and rinsed with filtered, distilled water. The resulting THP treated primed substrate was immersed in a solution of 50 mM solution of silver nitrate for about 16 hours, with mild agitation. The substrate was removed from the solution of silver nitrate and rinsed with filtered, distilled water. Any reducing groups on the compound including a trihydroxyphenyl group would be expected to reduce the silver nitrate if the THP was coupled to the primed substrate. It was found that the THP had reduced the silver ions to silver nanoparticles resulting in a brown color to the polysulfone substrate.

Thus, Example 9 corroborates the confirmation of the immobilization of assorted THP groups onto a polysulfone substrate according to the invention, via the coupling of THP to chitooligosaccharide while maintaining its reactivity.

Example 10

Alcian Blue Test for Confirming the Immobilization of Heparin on a Substrate

An antithrombogenic agent, heparin, was immobilized onto a polycarbonate substrate. A polycarbonate substrate was immersed in a solution of chitooligosaccharide primer compound (1 mg/mL, 10,000 Mw) dissolved in 10 mM Bicine buffer (pH of 8.0). The solution with the polycarbonate substrate immersed therein was mildly agitated at room temperature for 24 hours. The substrate was removed from the solution and rinsed with filtered, distilled water. The resulting primed substrate was immersed in a solution of gallic acid (2 mg/mL) in 100 mM Bicine buffer (pH 7.5). The gallic acid solution with the primed-substrate immersed therein was mildly agitated at room temperature for 24 hours. The substrate was removed from the gallic acid solution and rinsed with filtered, distilled water. The resulting gallic acid treated primed substrate was immersed in a solution of heparin (1 mg/mL) in 0.3 M sodium acetate and 0.6 M sodium chloride solution. The solution of heparin with the gallic acid treated primed substrate immersed therein was mildly agitated for about 24 hours. The substrate was removed from the solution of heparin and rinsed with filtered, distilled water. The resulting polycarbonate substrate with heparin immobilized on the surface thereof was immersed in a solution of Alcian blue for about 3 hours, with mild agitation. The substrate was removed from the solution of Alcian blue and rinsed with filtered, distilled water. Any anionic active agents, such as heparin, immobilized on the substrate would be expected to complex with the cationic Alcian blue dye. It was found that the heparin formed a complex with the Alcian blue, resulting in a blue stain to the polysulfone substrate.

Thus, Example 10 illustrates the confirmation of the immobilization of heparin onto a polycarbonate substrate according to the invention.

Example 11

Immobilization of Polyethylene Glycol on Polysulfone Substrate

An antifouling agent, polyethylene glycol (PEG), is immobilized onto polysulfone substrate. A polysulfone substrate is immersed in a solution of chitooligosaccharide primer compound (1 mg/mL, 10,000 Mw) dissolved in 10 mM Bicine (pH 8.4). The solution with the polysulfone substrate immersed therein is mildly agitated at room temperature for 24 hours. The substrate is removed from the solution and rinsed with filtered, distilled water. The resulting primed substrate is immersed in a solution of gallic acid (2.5 mg/mL) dissolved in 100 mM Bicine (pH 7.7). The gallic acid solution with the primed-substrate immersed therein is mildly agitated at room temperature for 24 hours. The substrate is removed from the gallic acid solution and rinsed with filtered, distilled water. The resulting gallic acid treated primed substrate is immersed in a solution of NH2-terminated PEG, SH-terminated PEG, and/or NHS-terminated PEG (1 mg/mL, 5,000 MW) in 0.3M sodium acetate and 0.6 M sodium chloride solution (pH 5.17). The solution of PEG with the gallic acid treated primed substrate immersed therein is mildly agitated for 24 hours. The substrate is removed from the solution of PEG and rinsed with filtered, distilled water, resulting in a polysulfone substrate with PEG immobilized on the surface thereof.

Thus, Example 11 illustrates how the immobilization of polyethylene glycol onto a polysulfone substrate can be achieved according to the invention.

Example 12

Immobilization of Polyvinylpyrrolidone on Polysulfone Substrate

An antifouling agent, polyvinylpyrrolidone (PVP), is immobilized onto polysulfone substrate. A polysulfone substrate is immersed in a solution of chitooligosaccharide primer compound (1 mg/mL, 10,000 Mw) dissolved in 10 mM Bicine (pH 8.4). The solution with the polysulfone substrate immersed therein is mildly agitated at room temperature for 24 hours. The substrate is removed from the solution and rinsed with filtered, distilled water. The resulting primed substrate is immersed in a solution of gallic acid (2.5 mg/mL) dissolved in 100 mM Bicine (pH 7.7). The gallic acid solution with the primed-substrate immersed therein is mildly agitated at room temperature for 24 hours. The substrate is removed from the gallic acid solution and rinsed with filtered, distilled water. The resulting gallic acid treated primed substrate is immersed in a solution of NH2- terminated PVP (1 mg/mL, 5,000 MW) in 10 mM Bicine (pH 8.5). The solution of PVP with the gallic acid treated primed substrate immersed therein is mildly agitated for up to 24 hours at ambient temperature. The substrate is removed from the solution of PVP and rinsed with filtered, distilled water, resulting in a polysulfone substrate with PVP immobilized on the surface thereof.

Thus, Example 12 illustrates how the immobilization of polyvinylpyrrolidone onto a polysulfone substrate can be achieved according to the invention.

Of course, other active agents, linker compounds, and compounds including trihydroxyphenyl groups could be used in the foregoing procedures.

What is claimed:

1. A method of immobilizing an active agent on a substrate surface, comprising the steps of:
   depositing a primer compound on a substrate, thereby forming a primed substrate;
   contacting the primed substrate with a solution of a compound including a trihydroxyphenyl group, thereby forming a trihydroxyphenyl-treated primed substrate; and
   contacting the trihydroxyphenyl-treated primed substrate with a solution of an active agent, thereby forming a substrate with an active agent immobilized on the surface thereof, wherein the compound including a trihydroxyphenyl group is selected from the group consisting of gallic acid, phloroglucinol carboxylic acid, gallamide, 5-methyl-benzene-1,2,3-triol, 3,4,5-trihydroxybenzaldehyde, 2,3,4-trihydroxybenzaldehyde, gallacetophenone, 3,4,5-trihydroxybenzamide, 2,3,4-trihydroxybenzoic acid, 5-hydroxydopamine hydrochloride, methyl gallate, pyrogallol, salts of the foregoing, and combinations thereof.

2. The method of claim 1, further comprising the step of contacting the trihydroxyphenyl-treated primed substrate with a solution of a linker compound thereby coupling the linker compound to the trihydroxyphenyl group and/or the primer compound of the trihydroxyphenyl-treated primed substrate, prior to contacting the trihydroxyphenyl-treated substrate with the solution of active agent.

3. The method of claim 1, wherein the substrate is selected from the group consisting of metal substrates, inorganic oxide substrates, ceramic substrates, polymer substrates, semiconductor substrates and combinations thereof.

4. The method of claim 1, further comprising the step of modifying the surface of the substrate prior to contacting the substrate with the solution of the primer compound.

5. The method of claim 1, wherein the substrate comprises a surface of a medical device or medical device component.

6. The method of claim 5, wherein the medical device comprises an extracorporeal blood circuit or components of an extracorporeal blood circuit.

7. The method of claim 1, wherein the primer compound is selected from the group consisting of oligosaccharides, polyamines, amino functionalized silanes, mercaptosilanes, and combinations thereof.

8. The method of claim 1, wherein the active agent is selected from the group consisting of antimicrobial agents, antifouling agents, anti-inflammatory agents, antithrombogenic agents, and combinations thereof.

9. The method of claim 1, wherein the active agent is selected from the group consisting of chitosan, linear polyethylene glycol, looped polyethylene glycol, polyethylene glycol derivatives, fractionated heparin, unfractionated heparin, heparin derivatives, quaternary ammonium polymers, albumin, polyethylenimine, 4-hydroxycoumarin derivatives, and combinations of the foregoing.

10. A method of immobilizing an active agent on a substrate surface, comprising the steps of:
    depositing a primer compound on the substrate thereby forming a primed substrate;
    combining in solution a compound including a trihydroxyphenyl group and an active agent, thereby forming a solution of an active agent-trihydroxyphenyl conjugate; and
    contacting the primed substrate with the solution of the active agent-trihydroxyphenyl conjugate, thereby coupling the trihydroxyphenyl group of the active agent-trihydroxyphenyl conjugate to the primed substrate and forming a substrate with an active agent immobilized on the surface thereof, wherein the compound including a trihydroxyphenyl group is selected from the group consisting of gallic acid, phloroglucinol carboxylic acid, gallamide, 5-methyl-benzene-1,2,3-triol, 3,4,5-trihydroxybenzaldehyde, 2,3,4-trihydroxybenzaldehyde, gallacetophenone, 3,4,5-trihydroxybenzamide, 2,3,4-trihydroxybenzoic acid, 5-hydroxydopamine hydrochloride, methyl gallate, pyrogallol, salts of the foregoing, and combinations thereof.

11. The method of claim 10, further comprising the step of contacting the trihydroxyphenyl-treated primed substrate with a solution of a linker compound thereby coupling the linker compound to the trihydroxyphenyl group and/or the primer compound of the trihydroxyphenyl-treated primed substrate, prior to contacting the trihydroxyphenyl-treated substrate with the solution of active agent.

12. The method of claim 10, wherein the substrate is selected from the group consisting of metal substrates, inorganic oxide substrates, ceramic substrates, polymer substrates, semiconductor substrates and combinations thereof.

13. The method of claim 10, further comprising the step of modifying the surface of the substrate prior to contacting the substrate with the solution of the primer compound.

14. The method of claim 10, wherein the substrate comprises a surface of a medical device or medical device component.

15. The method of claim 14, wherein the medical device comprises an extracorporeal blood circuit or components of an extracorporeal blood circuit.

16. The method of claim 10, wherein the primer compound is selected from the group consisting of oligosaccharides, polyamines, amino functionalized silanes, mercaptosilanes, and combinations thereof.

17. The method of claim 10, wherein the active agent is selected from the group consisting of antimicrobial agents, antifouling agents, anti-inflammatory agents, antithrombogenic agents, and combinations thereof.

18. The method of claim 10, wherein the active agent is selected from the group consisting of chitosan, linear polyethylene glycol, looped polyethylene glycol, polyethylene glycol derivatives, fractionated heparin, unfractionated heparin, heparin derivatives, quaternary ammonium polymers, albumin, polyethylenimine, 4-hydroxycoumarin derivatives, and combinations of the foregoing.

19. The method of claim 10, wherein the solution of the primer compound is at a pH in a range of about 7.5 to about 9.5.

* * * * *